(12) United States Patent
Depré et al.

(10) Patent No.: US 12,030,887 B2
(45) Date of Patent: Jul. 9, 2024

(54) SYNTHETIC METHODS OF MAKING FUSED HETEROCYCLIC COMPOUNDS AS OREXIN RECEPTOR MODULATORS

(71) Applicant: Janssen Pharmaceutica NV, Beerse (BE)

(72) Inventors: Dominique Paul Michel Depré, Beerse (BE); Kiran Matcha, Beerse (BE); Andy Josephina Joannes Huygaerts, Beerse (BE); Luc Jozef Raphael Moens, Beerse (BE); Dinesh Gala, Raritan, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 647 days.

(21) Appl. No.: 17/293,291

(22) PCT Filed: Nov. 11, 2019

(86) PCT No.: PCT/IB2019/059677
§ 371 (c)(1),
(2) Date: May 12, 2021

(87) PCT Pub. No.: WO2020/100011
PCT Pub. Date: May 22, 2020

(65) Prior Publication Data
US 2022/0009932 A1 Jan. 13, 2022

Related U.S. Application Data

(60) Provisional application No. 62/760,995, filed on Nov. 14, 2018.

(51) Int. Cl.
C07D 487/04 (2006.01)

(52) U.S. Cl.
CPC .................. C07D 487/04 (2013.01)

(58) Field of Classification Search
CPC .................................................. C07D 487/04
See application file for complete search history.

(56) References Cited

U.S. PATENT DOCUMENTS

| 8,653,263 B2 * | 2/2014 | Chai ................ A61P 1/12 |
| | | 546/159 |
| 2002/0019388 A1 | 2/2002 | Schrimpf et al. |
| 2005/0065178 A1 | 3/2005 | Basha et al. |
| 2005/0101602 A1 | 5/2005 | Basha et al. |
| 2006/0258672 A1 | 11/2006 | Barbosa et al. |
| 2013/0137672 A1 | 5/2013 | Branstetter et al. |
| 2014/0171430 A1 | 6/2014 | Etavic et al. |
| 2017/0258790 A1 | 9/2017 | De Boer et al. |

FOREIGN PATENT DOCUMENTS

| TW | 201141859 A | 12/2011 |
| WO | 95/15327 A1 | 6/1995 |
| WO | 2001/081347 A2 | 11/2001 |
| WO | 2006/123121 A1 | 11/2006 |
| WO | 2006/124897 A2 | 11/2006 |
| WO | 2008/067121 A2 | 6/2008 |
| WO | 2009/081197 A1 | 7/2009 |
| WO | 2015/150252 A1 | 10/2015 |
| WO | 2018/146466 A1 | 8/2018 |

OTHER PUBLICATIONS

RN: 1941655-07-7, "Pyrrolo[3,4-c]pyrrole-1,3(2H, 3aH)-dione, 5-(4,6-diethyl-2-pyrimidinyl)tetrahydro-, (3aR,6aS)", Chemcats, Jun. 29, 2016, 1 page.
Huang et al., "Practical Asymmetric Synthesis of RO5114436, a CCR5 Receptor Antagonist", Organic Process Research & Development, Oct. 3, 2010, vol. 14, Issue 3, pp. 592-599.
Joucla et al., "Parent and N-substituted azomethine ylides from a-amino acids and formaldehyde: An easy access to 2,5-unsubstituted pyrrolidines. Evidence for oxazolidin-5-ones as direct precursor of these reactive intermediates", Bulletin de la Societe Chimique de France, May 31, 1988, vol. 1988, Issue 3, pp. 579-583.
Letavic et al., "Novel Octahydropyrrolo[3,4-c]pyrroles Are Selective Orexin-2 Antagonists: SAR Leading to a Clinical Candidate", J. Med. Chem., Jun. 18, 2015, vol. 58, Issue 14, pp. 5620-5636.
Manka et al., "Octahydropyrrolo[3,4-c]pyrrole negative allosteric modulators of mGlu1", Bioorg Med Chem Lett., Jul. 23, 2013, vol. 23, Issue 18, pp. 5091-5096.
McAlpine et al., "Synthesis of Small 3-Fluoro- and 3,3-Difluoropyrrolidines Using Azomethine Ylide", Chemistry. J. Org. Chem., Jun. 9, 2015, vol. 80, No. 14, pp. 7266-7274.
Tsuge et al., "Simple generation of nonstabilized azomethine ylides through decarboxylative condensation of a-amino acids with carbonyl compounds via 5-oxazolidinone intermediates", Bulletin of the Chemical Society of Japan, Nov. 30, 1987, vol. 60, Issue 11, pp. 4079-4089.

(Continued)

Primary Examiner — Timothy R Rozof
(74) Attorney, Agent, or Firm — BakerHostetler

(57) ABSTRACT

Processes for preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl) methanone are described, which are useful for commercial manufacturing. Said compound is an orexin receptor modulator and may be useful in pharmaceutical compositions and methods for the treatment of diseased states, disorders, and conditions mediated by orexin activity, such as insomnia and depression.

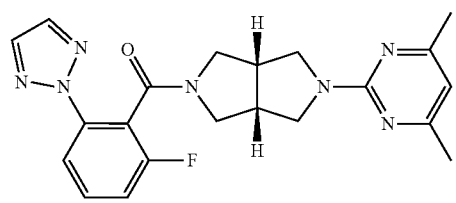

15 Claims, No Drawings

(56) References Cited

OTHER PUBLICATIONS

Oldham, MD, "5-Oxazolidinones: Key Intermediates to Peptidomimetics with Latent Reactivity and Conformational Restriction," Doctoral Thesis, University of Canterbury, pp. 1-63, 1997.
PubChem CID 101510576, pp. 1-6, Create Date: Dec. 18, 2015; p. 2.
PubChem CID 128564374, pp. 1-7, Create Date: Jun. 18, 2017; p. 2.
PubChem CID 1514449, pp. 1-11, Create Date: Jul. 11, 2005; p. 2.
PubChem CID 21867682, pp. 1-12, Create Date: Dec. 5, 2007; p. 2.
PubChem CID 312674, pp. 1-12, Create Date: Mar. 26, 2005; p. 2.
PubChem CID 59486002, pp. 1-9, Create Date: Aug. 20, 2012; p. 2.
Belskaya et al., "Synthesis of 2H-1,2,3-Triazoles", Topics Heterocycl. Chem., 2015, vol. 40, pp. 51-116.
Frost et al., "Synthesis and Structure-Activity Relationships of 3,8-Diazabicyclo[4.2.0]octane Ligands, Potent Nicotinic Acetylcholine Receptor Agonists", Journal of Medicinal Chemistry, 2006, vol. 49 No. 26, pp. 7843-7853.
Green et al., Protective Groups in Organic Synthesis, Wiley-Interscience, New York, 1999, pp. 579-580 & 744-747.
Myachina, "Optimization of the synthesis of 2-phenyl-1,2,3-triazole", Chemistry of Heterocyclic Compounds, 2010, vol. 46 No. 1, pp. 79-81.
Peyron et al., "Neurons Containing Hypocretin (Orexin) Project to Multiple Neuronal Systems", J. Neurosci., 1998, vol. 18 No. 23, pp. 9996-10015.
Potkin et al., "Synthesis of 3-amino-4,5-dichloroisothiazole", Russian Journal of Organic Chemistry, Dec. 2009, vol. 45 No. 4, pp. 555-558.
Riebsomer, "2-PHENYL-2,1,3-Triazole and Derivatives", J. Org. Chem., 1948, vol. 13, pp. 815-821.
Roth et al., "Highly Selective Synthesis of 2-(2H-1,2,3-Triazol-2-yl)benzoic Acids", OPRD 2019, vol. 23, pp. 234-243.
Talapatra et al, "Synthesis of Heterocycles. I: N-Iodosuccinimide, A Convenient oxidative cyclising agent in the synthesis of oxazole, isoxazole, benzofuran, furoxan and 1,2,3-Triazole-1-Oxide Derivatives", Heterocycles, 1980, vol. 14 No. 9, pp. 1279-1282.
Tome, Science of Synthesis, 2004, Section 13.13.2, pp. 528-540.
Ueda et al., "Highly N2-Selective Palladium-Catalyzed Arylation of 1,2,3-Triazoles", Angew. Chem. Int. Ed., 2011, vol. 50 No. 38, pp. 8944-8947.
Van Den Pol et al., "Hypothalamic Hypocretin (Orexin): Robust Innervation of the Spinal Cord", J. Neuroscience, 1999, vol. 19 No. 8, pp. 3171-3182.
Wang et al., "Highly Regioselective N-2 Arylation of 4,5-Dibromo-1,2,3-triazole: Efficient Synthesis of 2-Aryltriazoles", Org. Let., 2009, vol. 11 No. 21, pp. 5026-5028.
PubChem CID 108125092, (3aR,6aS)-5-(4,6-dimethylpyrimidin-2-yl)-2,3,3a,4,6,6a-hexahydro-1H-pyrrolo[3,4-c]pyrrole, Jan. 15, 2016, 10 Pages.
PubChem CID 124416753, (3aS,6aS)-2-benzyl-5-pyrimidin-2-yl-1,3,3a,4,6,6a-hexahydropyrrolo[3,4-c]pyrrole, Apr. 10, 2017, 9 Pages.

\* cited by examiner

SYNTHETIC METHODS OF MAKING FUSED HETEROCYCLIC COMPOUNDS AS OREXIN RECEPTOR MODULATORS

CROSS-REFERENCE TO RELATED APPLICATIONS

This application is the National Stage of International Patent Application No. PCT/IB2019/059677, filed Nov. 11, 2019, which claims the benefit of U.S. Provisional Patent Application No. 62/760,995, filed Nov. 14, 2018, the contents of which are incorporated herein by reference.

FIELD OF THE INVENTION

The present invention relates to the synthesis methods making (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone, a compound useful for modulation of the orexin receptor and for the treatment of disease states, disorders, and conditions mediated by orexin receptor activity.

BACKGROUND OF THE INVENTION

Orexin (or hypocretin) signaling is mediated by two receptors and two peptide agonists. The two orexin peptides (orexin A and orexin B) herein after referred to as orexins, bind to two high affinity receptors, termed orexin-1 and orexin-2 receptors. The orexin-1 receptor is selective in favor of orexin A, while the orexin-2 receptor binds both orexins with similar affinities. The orexins, are cleavage products of the same gene, prepro orexin. In the central nervous system neurons expressing prepro-orexin, the precursor from which orexin is produced, are found in the perifornical nucleus, the dorsal hypothalamus and the lateral hypothalamus (C. Peyron et al., *J. Neurosci.*, 1998, 18(23), 9996-10015). Orexinergic cells in these nuclei project to many areas of the brain, extending rostrally to the olfactory bulbs and caudally to the spinal cord (van den Pol, A. N. et al., *J. Neuroscience.*, 1999, 19(8), 3171-3182).

Citation of a reference herein shall not be construed as an admission that such reference is prior art to the present invention. All publications referred to herein are incorporated by reference in their entireties.

Substituted diaza-bicyclic compounds have been reported as active central nervous system agents (International Publication No. WO2001081347, Nov. 1, 2001; US2002/0019388, Feb. 14, 2002), a7 acetylcholine receptor modulators (US2005/101602, May 12, 2005; US2005/0065178, Mar. 24, 2005 and Frost et al, *Journal of Medicinal Chemistry*, 2006, 49(26), 7843-7853), proline transporter inhibitors for the treatment of cognitive impairment (WO2008067121, Jun. 5, 2008) and for improving cognition (WO 2006 124897, Nov. 23, 2006 and US20060258672, Nov. 16, 2006), as androgen receptor ligands for the treatment of androgen receptor associated conditions including cancer (WO2009081197, Jul. 2, 2009), and as histone deacetylase inhibitors for the treatment of cancers, neurodegenerative diseases and autoimmune diseases (WO20060123121, Nov. 23, 2006).

Among the developed compounds, (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone was found to act as an inhibitor of the orexin-2 receptor and to be useful for the treatment of sleep disorders and major depressive diseases (U.S. Pat. No. 8,653,263 B2). The original synthesis had a linear sequence of eight steps from commercially available 1-benzyl-1H-pyrrole-2,5-dione, including four protecting group manipulation steps (scheme below).

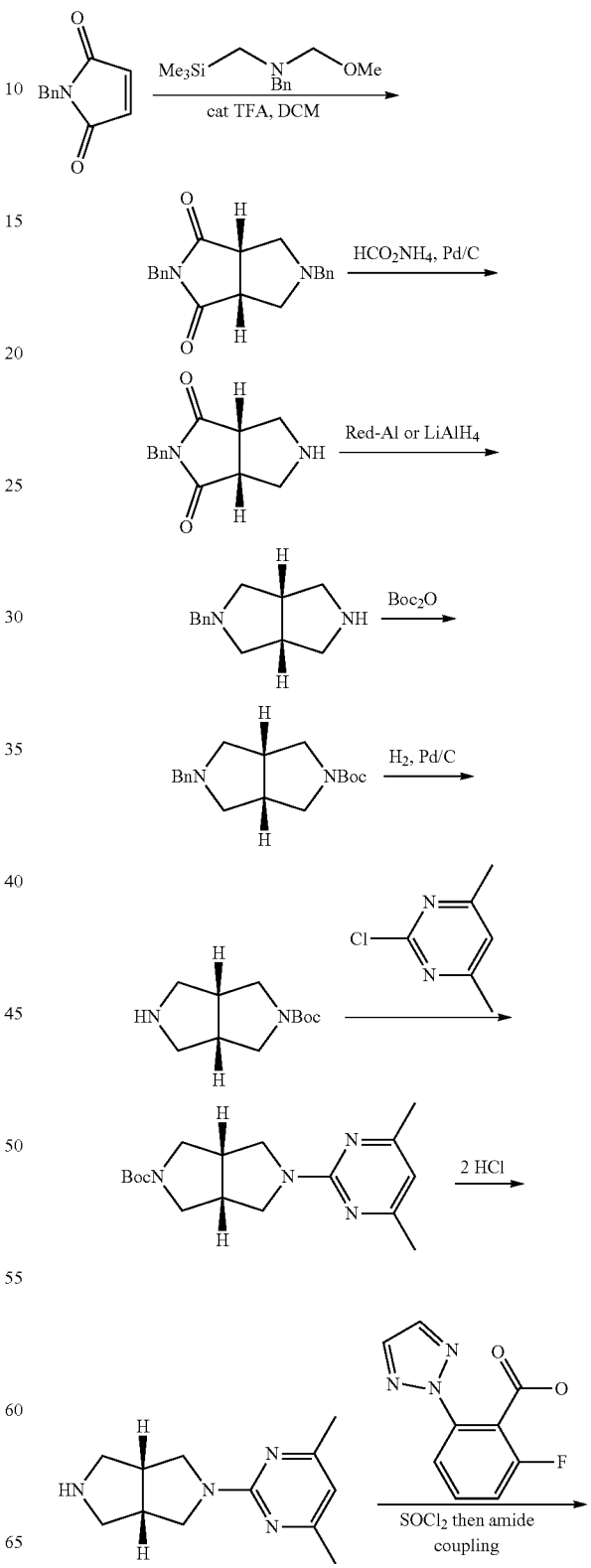

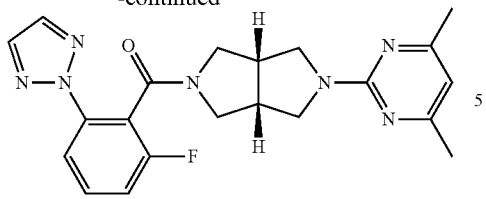

Other multi-step efforts to make the (3aR,6aS)-2-benzyl-octahydropyrrolo[3,4-c]pyrrole intermediate,

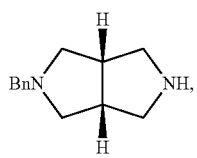

have been reported (*Org. Proc. Res. Dev.* 2010, 18, 592, and *J. Med. Chem.* 2015, 58, 5620). However, an improved synthesis was required for economical commercial production of (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone.

It is an object of the invention to provide a process for preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone utilizing fewer protecting group steps and a shorter overall reaction sequence in order to reduce cost of manufacturing.

SUMMARY OF THE INVENTION

The invention comprises a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

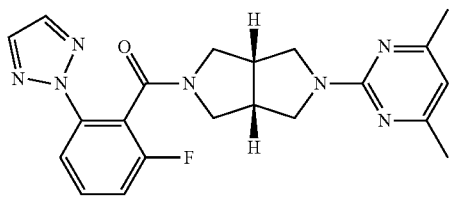 [SMILES: Cc1cc(C)nc(N2C[C@H]3CN(C(=O)c4c(F)cccc4-n4nccn4)C[C@H]3C2)n1]

Wherein early installation of the 4,6-dimethylpyrimid-2-yl group obviates the need for three protecting group manipulation steps, reducing the linear sequence from commercially available 1-benzyl-1H-pyrrole-2,5-dione to four steps.

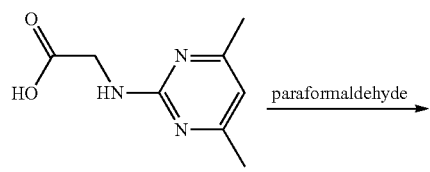

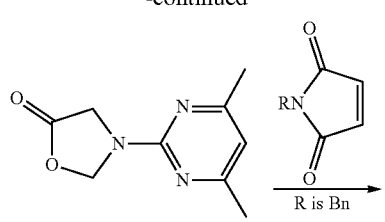

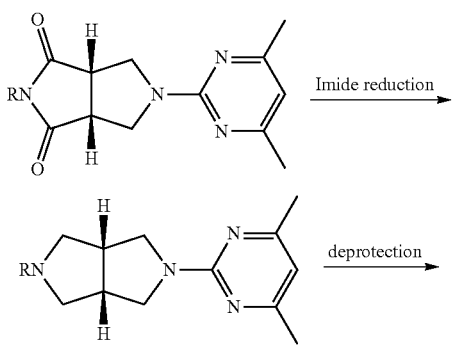

In other embodiments of the invention, protecting groups are eliminated altogether, and the linear sequence from commercially available 1H-pyrrole-2,5-dione is reduced to as few as three steps.

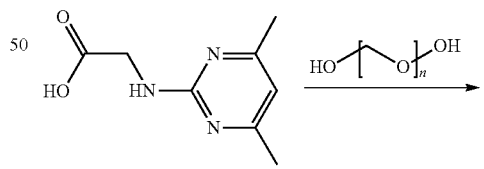

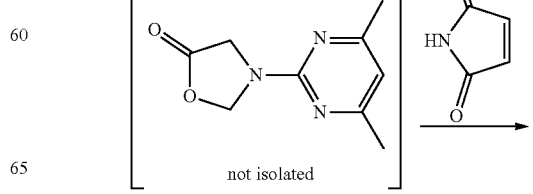

-continued

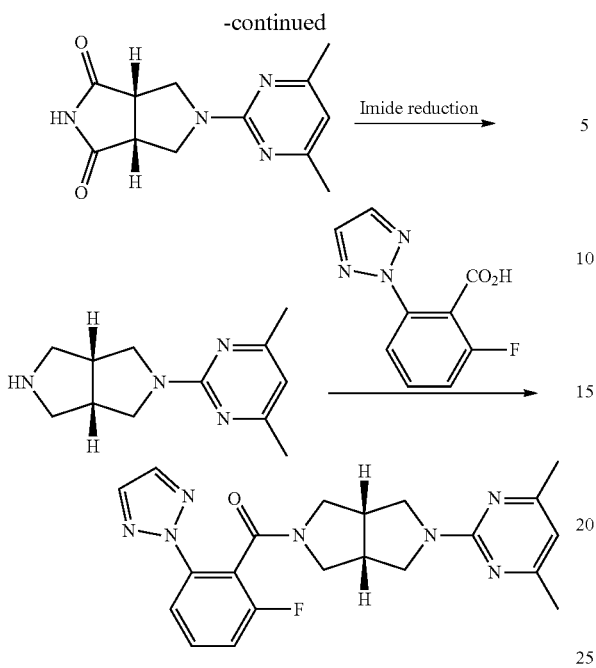

The invention comprises a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

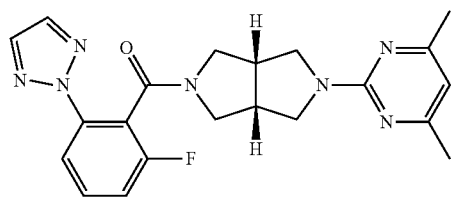 [SMILES: Cc1cc(C)nc(N2C[C@H]3CN(C(=O)c4c(F)cccc4-n4nccn4)C[C@H]3C2)n1]

said process comprising step described below:

a) Oxazolidination of (4,6-dimethylpyrimidin-2-yl)glycine,

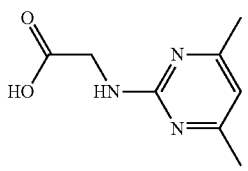

wherein said oxazolidination is characterized by the use of formaldehyde or paraformaldehyde to obtain 3-(4,6-dimethylpyrimidin-2-yl)oxazolidin-5-one

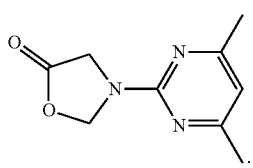

DETAILED DESCRIPTION OF THE INVENTION

The invention comprises a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

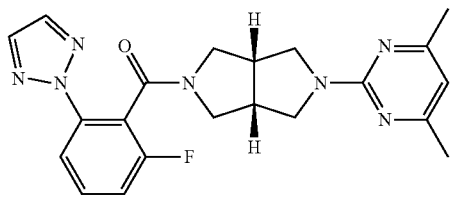 [SMILES: Cc1cc(C)nc(N2C[C@H]3CN(C(=O)c4c(F)cccc4-n4nccn4)C[C@H]3C2)n1]

said process comprising step described below:

a) Oxazolidination of (4,6-dimethylpyrimidin-2-yl)glycine,

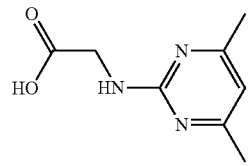

wherein said oxazolidination is characterized by the use of formaldehyde or paraformaldehyde to obtain 3-(4,6-dimethylpyrimidin-2-yl)oxazolidin-5-one

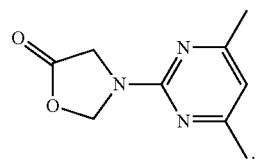

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

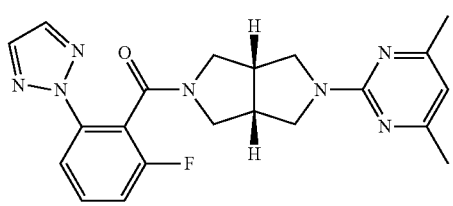 [SMILES: Cc1cc(C)nc(N2C[C@H]3CN(C(=O)c4c(F)cccc4-n4nccn4)C[C@H]3C2)n1]

said process comprising the steps described below:

a) Oxazolidination of (4,6-dimethylpyrimidin-2-yl)glycine,

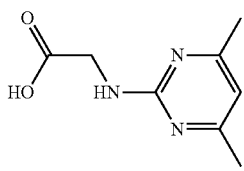

wherein said oxazolidination is characterized by the use of formaldehyde or paraformaldehyde to obtain 3-(4,6-dimethylpyrimidin-2-yl)oxazolidin-5-one

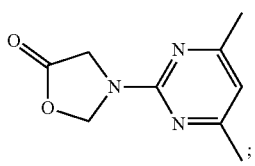

b) Reaction of 3-(4,6-dimethylpyrimidin-2-yl)oxazolidin-5-one

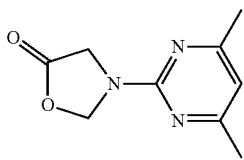

with 1-benzyl-1H-pyrrole-2,5-dione

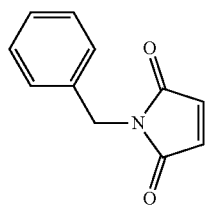 [SMILES: O=C1C=CC(=O)N1Cc1ccccc1]

at a temperature greater than 250° C. to form (3aR,6aS)-2-benzyl-5-(4,6-dimethylpyrimidin-2-yl)tetrahydropyrrolo[3,4-c]pyrrole-1,3(2H,3aH)-dione

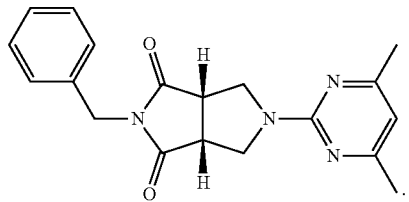 [SMILES: Cc1cc(C)nc(N2C[C@@H]3C(=O)N(Cc4ccccc4)C(=O)[C@@H]3C2)n1]

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

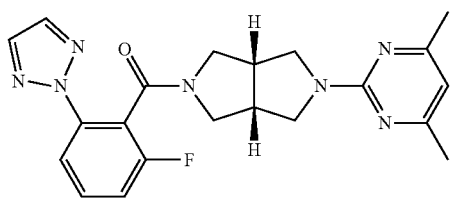 [SMILES: Cc1cc(C)nc(N2C[C@H]3CN(C(=O)c4c(F)cccc4-n4nccn4)C[C@H]3C2)n1]

said process comprising the steps described below:

a) Oxazolidination of (4,6-dimethylpyrimidin-2-yl)glycine,

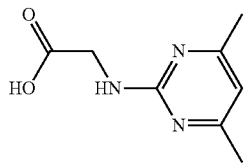

wherein said oxazolidination is characterized by the use of formaldehyde or paraformaldehyde to obtain 3-(4,6-dimethylpyrimidin-2-yl)oxazolidin-5-one

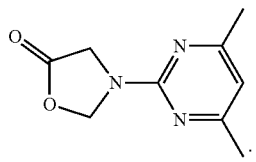

b) Reaction of 3-(4,6-dimethylpyrimidin-2-yl)oxazolidin-5-one

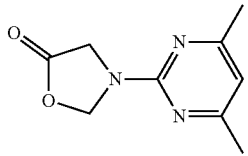

with 1-benzyl-1H-pyrrole-2,5-dione

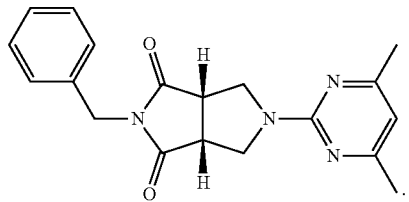 [SMILES: Cc1cc(C)nc(N2C[C@@H]3C(=O)N(Cc4ccccc4)C(=O)[C@@H]3C2)n1]

at a temperature greater than 250° C. to form (3aR,6aS)-2-benzyl-5-(4,6-dimethylpyrimidin-2-yl)tetrahydropyrrolo[3,4-c]pyrrole-1,3(2H,3aH)-dione

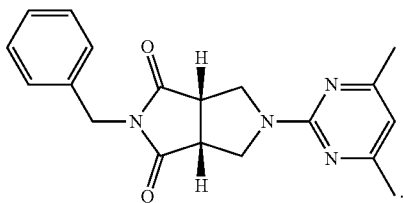

c) reduction of (3aR,6aS)-2-benzyl-5-(4,6-dimethylpy-rimidin-2-yl)tetrahydropyrrolo[3,4-c]pyrrole-1,3(2H,3aH)-dione

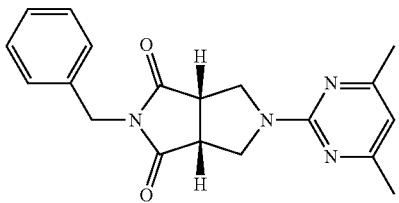 [SMILES: Cc1cc(C)nc(N2C[C@@H]3C(=O)N(Cc4ccccc4)C(=O)[C@@H]3C2)n1]

to form (3aR,6aS)-2-benzyl-5-(4,6-dimethylpyrimidin-2-yl)octahydropyrrolo[3,4-c]pyrrole

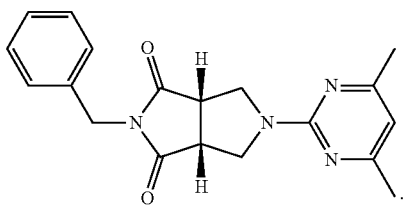 [SMILES: Cc1cc(C)nc(N2C[C@@H]3C(=O)N(Cc4ccccc4)C(=O)[C@@H]3C2)n1]

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

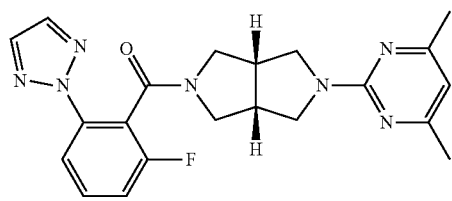 [SMILES: Cc1cc(C)nc(N2C[C@H]3CN(C(=O)c4c(F)cccc4-n4nccn4)C[C@H]3C2)n1]

said process comprising the steps described below:
a) Oxazolidination of (4,6-dimethylpyrimidin-2-yl)glycine,

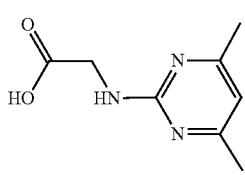

wherein said oxazolidination is characterized by the use of formaldehyde or paraformaldehyde to obtain 3-(4,6-dimethylpyrimidin-2-yl)oxazolidin-5-one b) Reaction of 3-(4,6-dimethylpyrimidin-2-yl)oxazolidin-5-one

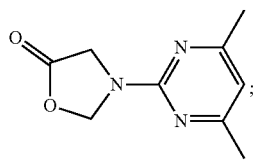

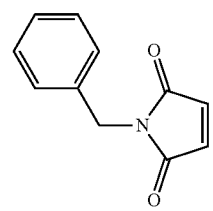 [SMILES: O=C1C=CC(=O)N1Cc1ccccc1]

with 1-benzyl-1H-pyrrole-2,5-dione at a temperature greater than 250° C. to form (3aR,6aS)-2-benzyl-5-(4,6-dimethylpyrimidin-2-yl)tetrahydropyrrolo[3,4-c]pyrrole-1,3(2H,3aH)-dione

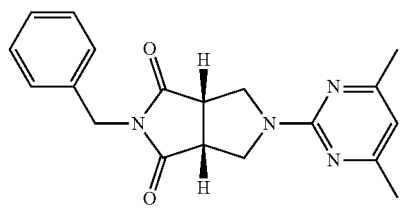 [SMILES: Cc1cc(C)nc(N2C[C@@H]3C(=O)N(Cc4ccccc4)C(=O)[C@@H]3C2)n1]

c) reduction of (3aR,6aS)-2-benzyl-5-(4,6-dimethylpy-rimidin-2-yl)tetrahydropyrrolo[3,4-c]pyrrole-1,3(2H,3aH)-dione to form (3aR,6aS)-2-benzyl-5-(4,6-dimethylpyrimidin-2-yl)octahydropyrrolo[3,4-c]pyrrole

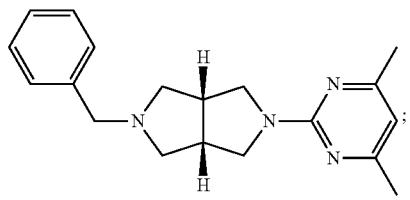 [SMILES: Cc1cc(C)nc(N2C[C@H]3CN(Cc4ccccc4)C[C@H]3C2)n1]

d) deprotection of (3aR,6aS)-2-benzyl-5-(4,6-dimethylpyrimidin-2-yl)octahydropyrrolo[3,4-c]pyrrole

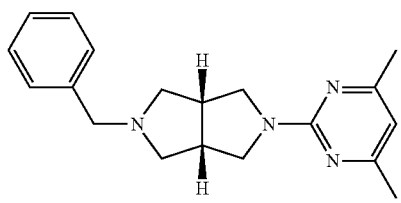 [SMILES: Cc1cc(C)nc(N2C[C@H]3CN(Cc4ccccc4)C[C@H]3C2)n1]

to form (3aR,6aS)-2-(4,6-dimethylpyrimidin-2-yl)octahydropyrrolo[3,4-c]pyrrole

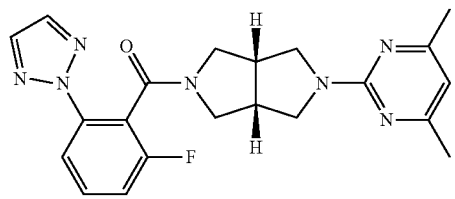 [SMILES: Cc1cc(C)nc(N2C[C@H]3CN(C(=O)c4c(F)cccc4-n4nccn4)C[C@H]3C2)n1]

by means of 10% (w/w) Pd/C and ammonium formate.

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

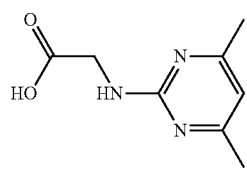

said process comprising the steps described below:

a) Oxazolidination of (4,6-dimethylpyrimidin-2-yl)glycine,

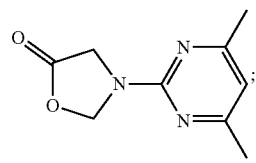

wherein said oxazolidination is characterized by the use of formaldehyde or paraformaldehyde to obtain 3-(4,6-dimethylpyrimidin-2-yl)oxazolidin-5-one b) Reaction of 3-(4,6-dimethylpyrimidin-2-yl)oxazolidin-5-one

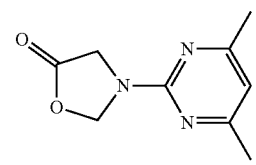

with 1-benzyl-1H-pyrrole-2,5-dione

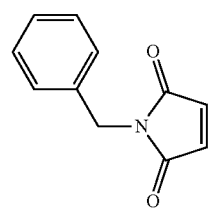 [SMILES: O=C1C=CC(=O)N1Cc1ccccc1]

at a temperature greater than 250° C. to form (3aR,6aS)-2-benzyl-5-(4,6-dimethylpyrimidin-2-yl)tetrahydropyrrolo[3,4-c]pyrrole-1,3(2H,3aH)-dione

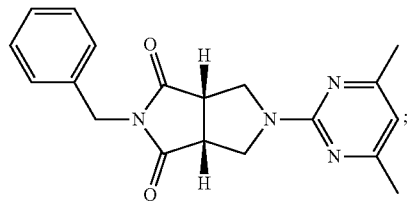 [SMILES: Cc1cc(C)nc(N2C[C@@H]3C(=O)N(Cc4ccccc4)C(=O)[C@@H]3C2)n1]

c) reduction of (3aR,6aS)-2-benzyl-5-(4,6-dimethylpyrimidin-2-yl)tetrahydropyrrolo[3,4-c]pyrrole-1,3(2H,3aH)-dione

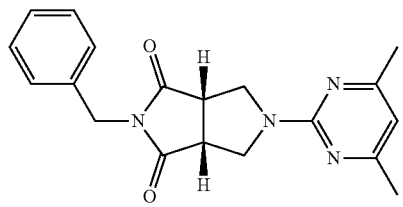 [SMILES: Cc1cc(C)nc(N2C[C@@H]3C(=O)N(Cc4ccccc4)C(=O)[C@@H]3C2)n1]

to form (3aR,6aS)-2-benzyl-5-(4,6-dimethylpyrimidin-2-yl)octahydropyrrolo[3,4-c]pyrrole

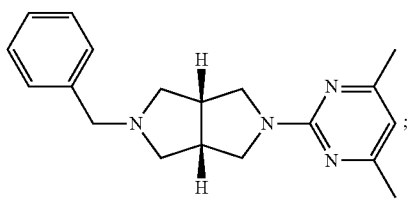 [SMILES: Cc1cc(C)nc(N2C[C@H]3CN(Cc4ccccc4)C[C@H]3C2)n1]

d) deprotection of (3aR,6aS)-2-benzyl-5-(4,6-dimethylpyrimidin-2-yl)octahydropyrrolo[3,4-c]pyrrole

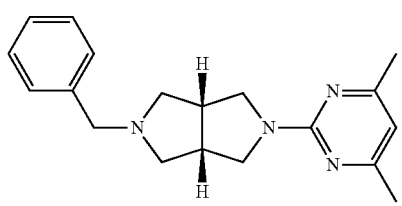 [SMILES: Cc1cc(C)nc(N2C[C@H]3CN(Cc4ccccc4)C[C@H]3C2)n1]

to form (3aR,6aS)-2-(4,6-dimethylpyrimidin-2-yl)octahydropyrrolo[3,4-c]pyrrole

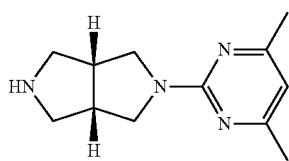 [SMILES: Cc1cc(C)nc(N2C[C@H]3CNC[C@H]3C2)n1]

by means of 10% (w/w) Pd/C and ammonium formate;

e) Amidation of (3aR,6aS)-2-(4,6-dimethylpyrimidin-2-yl)octahydropyrrolo[3,4-c]pyrrole

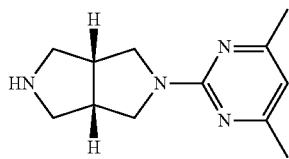 [SMILES: Cc1cc(C)nc(N2C[C@H]3CNC[C@H]3C2)n1]

with 2-fluoro-6-(2H-1,2,3-triazol-2-yl)benzoic acid

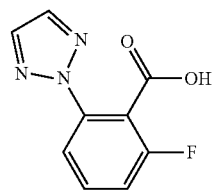 [SMILES: O=C(O)c1c(F)cccc1-n1nccn1]

by means of $SOCl_2$ to form (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

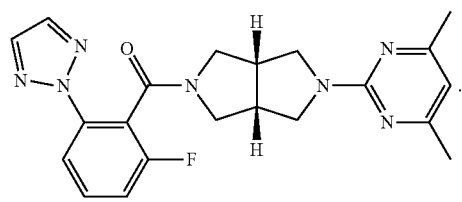 [SMILES: Cc1cc(C)nc(N2C[C@H]3CN(C(=O)c4c(F)cccc4-n4nccn4)C[C@H]3C2)n1]

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

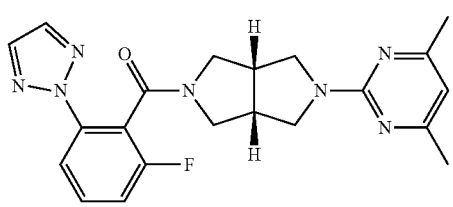 [SMILES: Cc1cc(C)nc(N2C[C@H]3CN(C(=O)c4c(F)cccc4-n4nccn4)C[C@H]3C2)n1]

said process comprising the steps described below:

a) Oxazolidination of (4,6-dimethylpyrimidin-2-yl)glycine,

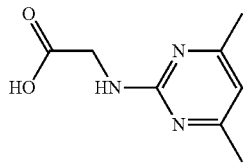

wherein said oxazolidination is characterized by the use of formaldehyde or paraformaldehyde to obtain 3-(4,6-dimethylpyrimidin-2-yl)oxazolidin-5-one

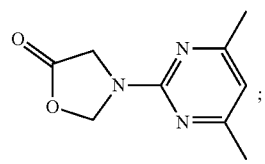

b) Reaction of 3-(4,6-dimethylpyrimidin-2-yl)oxazolidin-5-one

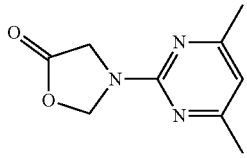

with 1H-pyrrole-2,5-dione

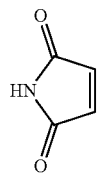

at a temperature greater than 250° C. to form (3aR,6aS)-5-(4,6-dimethylpyrimidin-2-yl)tetrahydropyrrolo[3,4-c]pyrrole-1,3(2H,3aH)-dione

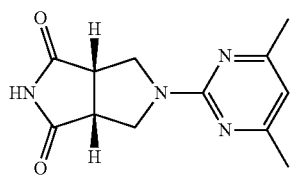

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

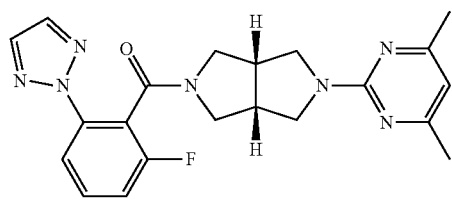 [SMILES: Cc1cc(C)nc(N2C[C@H]3CN(C(=O)c4c(F)cccc4-n4nccn4)C[C@H]3C2)n1]

said process comprising the steps described below:

a) Oxazolidination of (4,6-dimethylpyrimidin-2-yl)glycine,

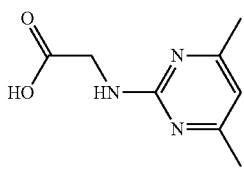

wherein said oxazolidination is characterized by the use of formaldehyde or paraformaldehyde to obtain 3-(4,6-dimethylpyrimidin-2-yl)oxazolidin-5-one

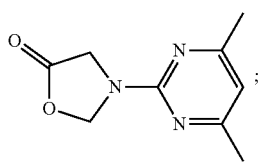

b) reaction of 3-(4,6-dimethylpyrimidin-2-yl)oxazolidin-5-one

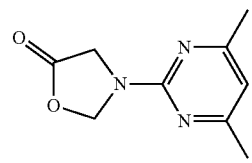

with 1H-pyrrole-2,5-dione

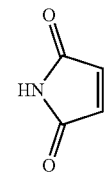

at a temperature greater than 250° C. to form (3aR,6aS)-5-(4,6-dimethylpyrimidin-2-yl)tetrahydropyrrolo[3,4-c]pyrrole-1,3(2H,3aH)-dione

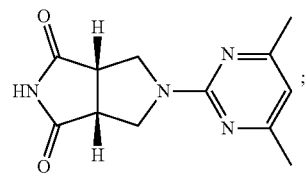 [SMILES: Cc1cc(C)nc(N2C[C@@H]3C(=O)NC(=O)[C@@H]3C2)n1]

c) reduction of (3aR,6aS)-5-(4,6-dimethylpyrimidin-2-yl)tetrahydropyrrolo[3,4-c]pyrrole-1,3(2H,3aH)-dione

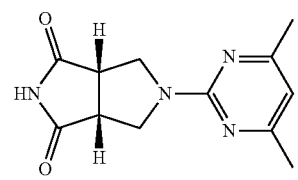 [SMILES: Cc1cc(C)nc(N2C[C@@H]3C(=O)NC(=O)[C@@H]3C2)n1]

to form (3aR,6aS)-2-(4,6-dimethylpyrimidin-2-yl)octahydropyrrolo[3,4-c]pyrrole

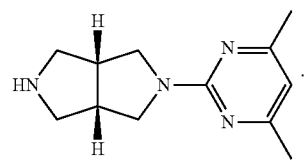 [SMILES: Cc1cc(C)nc(N2C[C@H]3CNC[C@H]3C2)n1]

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

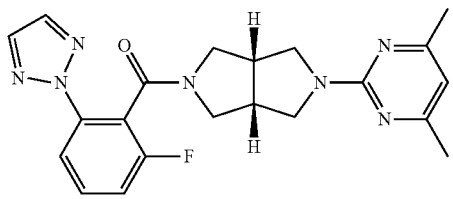 [SMILES: Cc1cc(C)nc(N2C[C@H]3CN(C(=O)c4c(F)cccc4-n4nccn4)C[C@H]3C2)n1]

said process comprising the steps described below:

a) Oxazolidination of (4,6-dimethylpyrimidin-2-yl)glycine,

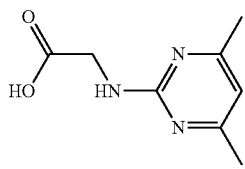

wherein said oxazolidination is characterized by the use of formaldehyde or paraformaldehyde to obtain 3-(4,6-dimethylpyrimidin-2-yl)oxazolidin-5-one

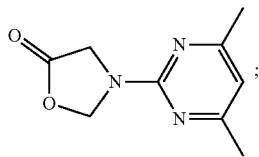

b) reaction of 3-(4,6-dimethylpyrimidin-2-yl)oxazolidin-5-one

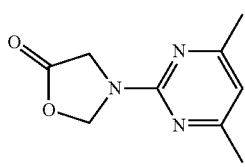

with 1H-pyrrole-2,5-dione

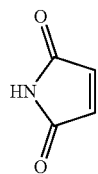

at a temperature greater than 250° C. to form (3aR,6aS)-5-(4,6-dimethylpyrimidin-2-yl)tetrahydropyrrolo[3,4-c]pyrrole-1,3(2H,3aH)-dione

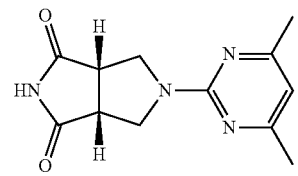

c) reduction of (3aR,6aS)-5-(4,6-dimethylpyrimidin-2-yl)tetrahydropyrrolo[3,4-c]pyrrole-1,3(2H,3aH)-dione

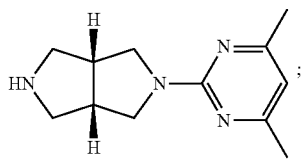 [SMILES: Cc1cc(C)nc(N2C[C@H]3CNC[C@H]3C2)n1]

to form (3aR,6aS)-2-(4,6-dimethylpyrimidin-2-yl)octahydropyrrolo[3,4-c]pyrrol

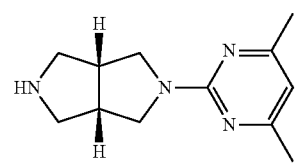 [SMILES: Cc1cc(C)nc(N2C[C@H]3CNC[C@H]3C2)n1]

e) Amidation of (3aR,6aS)-2-(4,6-dimethylpyrimidin-2-yl)octahydropyrrolo[3,4-c]pyrrole

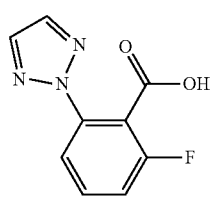 [SMILES: O=C(O)c1c(F)cccc1-n1nccn1]

with 2-fluoro-6-(2H-1,2,3-triazol-2-yl)benzoic acid

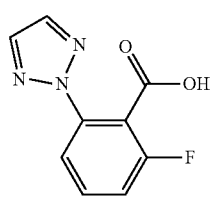 [SMILES: O=C(O)c1c(F)cccc1-n1nccn1]

by means of $SOCl_2$ to form (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

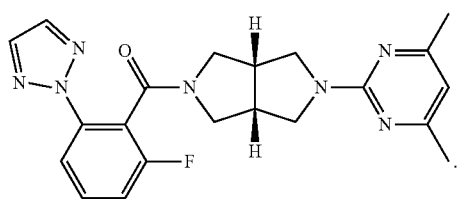 [SMILES: Cc1cc(C)nc(N2C[C@H]3CN(C(=O)c4c(F)cccc4-n4nccn4)C[C@H]3C2)n1]

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

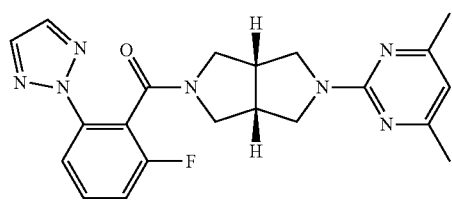 [SMILES: Cc1cc(C)nc(N2C[C@H]3CN(C(=O)c4c(F)cccc4-n4nccn4)C[C@H]3C2)n1]

said process comprising the steps described below:
a) Oxazolidination of (4,6-dimethylpyrimidin-2-yl)glycine,

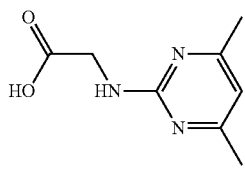

wherein said oxazolidination is characterized by the use of formaldehyde or paraformaldehyde to obtain 3-(4,6-dimethylpyrimidin-2-yl)oxazolidin-5-one

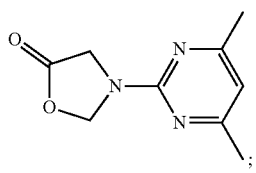

b) Reaction of 3-(4,6-dimethylpyrimidin-2-yl)oxazolidin-5-one

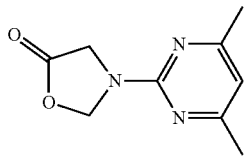

with 1-benzyl-1H-pyrrole-2,5-dione

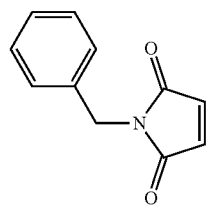 [SMILES: O=C1C=CC(=O)N1Cc1ccccc1]

at a temperature greater than 250° C. to form (3aR,6aS)-2-benzyl-5-(4,6-dimethylpyrimidin-2-yl)tetrahydropyrrolo[3,4-c]pyrrole-1,3(2H,3aH)-dione

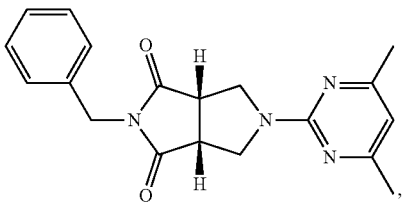 [SMILES: Cc1cc(C)nc(N2C[C@@H]3C(=O)N(Cc4ccccc4)C(=O)[C@@H]3C2)n1]

wherein said 3-(4,6-dimethylpyrimidin-2-yl)oxazolidin-5-one is not isolated prior to reaction with said 1-benzyl-1H-pyrrole-2,5-dione.

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

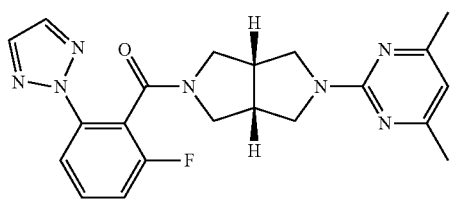 [SMILES: Cc1cc(C)nc(N2C[C@H]3CN(C(=O)c4c(F)cccc4-n4nccn4)C[C@H]3C2)n1]

said process comprising the steps described below:
a) Oxazolidination of (4,6-dimethylpyrimidin-2-yl)glycine,

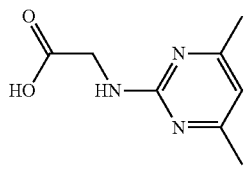

wherein said oxazolidination is characterized by the use of formaldehyde or paraformaldehyde to obtain 3-(4,6-dimethylpyrimidin-2-yl)oxazolidin-5-one

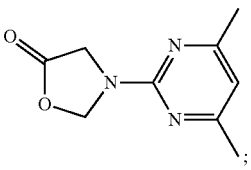

b) Reaction of 3-(4,6-dimethylpyrimidin-2-yl)oxazolidin-5-one

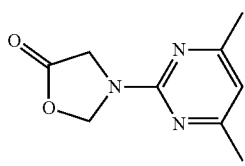

with 1-benzyl-1H-pyrrole-2,5-dione

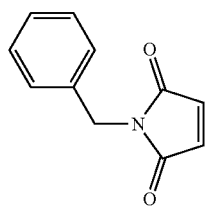 [SMILES: O=C1C=CC(=O)N1Cc1ccccc1]

at a temperature greater than 250° C. to form (3aR,6aS)-2-benzyl-5-(4,6-dimethylpyrimidin-2-yl)tetrahydropyrrolo[3,4-c]pyrrole-1,3(2H,3aH)-dione

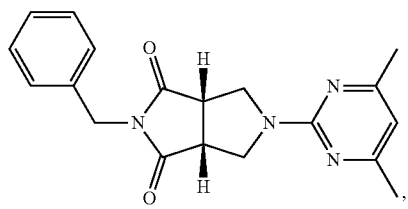 [SMILES: Cc1cc(C)nc(N2C[C@@H]3C(=O)N(Cc4ccccc4)C(=O)[C@@H]3C2)n1]

wherein said 3-(4,6-dimethylpyrimidin-2-yl)oxazolidin-5-one is isolated prior to reaction with said 1-benzyl-1H-pyrrole-2,5-dione.

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

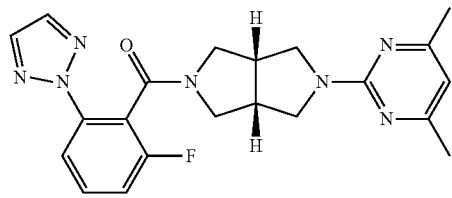 [SMILES: Cc1cc(C)nc(N2C[C@H]3CN(C(=O)c4c(F)cccc4-n4nccn4)C[C@H]3C2)n1]

said process comprising the steps described below:
a) Oxazolidination of (4,6-dimethylpyrimidin-2-yl)glycine,

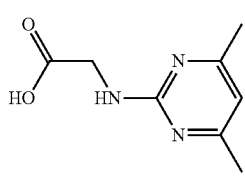

wherein said oxazolidination is characterized by the use of formaldehyde or paraformaldehyde to obtain 3-(4,6-dimethylpyrimidin-2-yl)oxazolidin-5-one

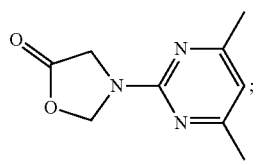

b) Reaction of 3-(4,6-dimethylpyrimidin-2-yl)oxazolidin-5-one

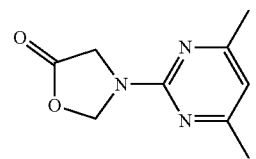

with 1H-pyrrole-2,5-dione

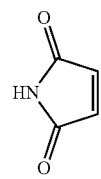

at a temperature greater than 250° C. to form (3aR,6aS)-5-(4,6-dimethylpyrimidin-2-yl)tetrahydropyrrolo[3,4-c]pyrrole-1,3(2H,3aH)-dione

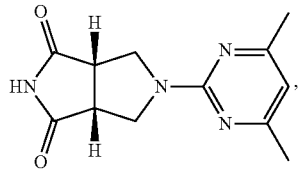 [SMILES: Cc1cc(C)nc(N2C[C@@H]3C(=O)NC(=O)[C@@H]3C2)n1]

wherein said 3-(4,6-dimethylpyrimidin-2-yl)oxazolidin-5-one is not isolated prior to reaction with said 1-benzyl-1H-pyrrole-2,5-dione.

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

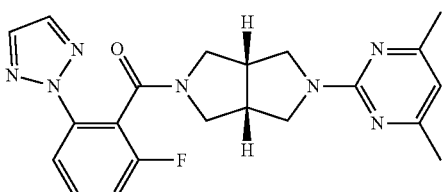

said process comprising the steps described below:
a) Oxazolidination of (4,6-dimethylpyrimidin-2-yl)glycine,

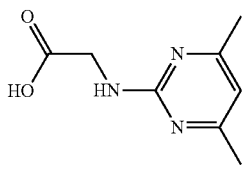

wherein said oxazolidination is characterized by the use of formaldehyde or paraformaldehyde to obtain 3-(4,6-dimethylpyrimidin-2-yl)oxazolidin-5-one

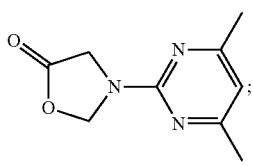

b) Reaction of 3-(4,6-dimethylpyrimidin-2-yl)oxazolidin-5-one

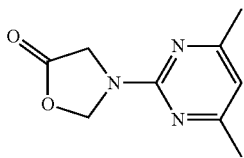

with 1H-pyrrole-2,5-dione

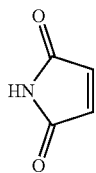

at a temperature greater than 250° C. to form (3aR,6aS)-5-(4,6-dimethylpyrimidin-2-yl)tetrahydropyrrolo[3,4-c]pyrrole-1,3(2H,3aH)-dione

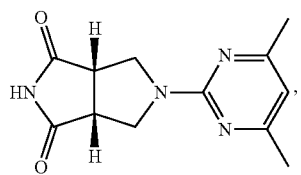

wherein said 3-(4,6-dimethylpyrimidin-2-yl)oxazolidin-5-one is isolated prior to reaction with said 1-benzyl-1H-pyrrole-2,5-dione.

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

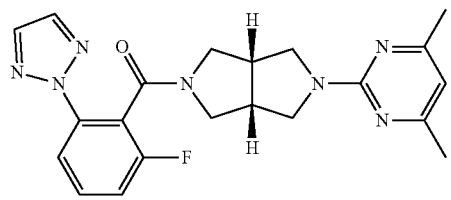 [SMILES: Cc1cc(C)nc(N2C[C@H]3CN(C(=O)c4c(F)cccc4-n4nccn4)C[C@H]3C2)n1]

said process comprising the steps described below:

a) Oxazolidination of (4,6-dimethylpyrimidin-2-yl)glycine,

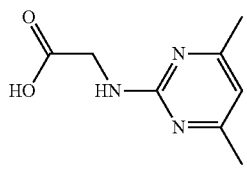

wherein said oxazolidination is characterized by the use of formaldehyde or paraformaldehyde to obtain 3-(4,6-dimethylpyrimidin-2-yl)oxazolidin-5-one

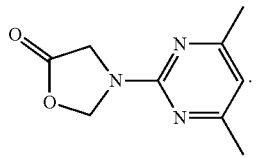

b) Reaction of 3-(4,6-dimethylpyrimidin-2-yl)oxazolidin-5-one

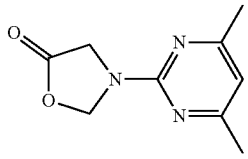

with 1-benzyl-1H-pyrrole-2,5-dione

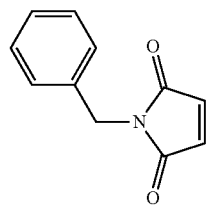 [SMILES: O=C1C=CC(=O)N1Cc1ccccc1]

at a temperature greater than 250° C. to form (3aR,6aS)-2-benzyl-5-(4,6-dimethylpyrimidin-2-yl)tetrahydropyrrolo[3,4-c]pyrrole-1,3(2H,3aH)-dione

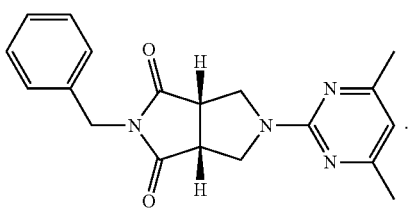 [SMILES: Cc1cc(C)nc(N2C[C@@H]3C(=O)N(Cc4ccccc4)C(=O)[C@@H]3C2)n1]

c) reduction of (3aR,6aS)-2-benzyl-5-(4,6-dimethylpyrimidin-2-yl)tetrahydropyrrolo[3,4-c]pyrrole-1,3(2H,3aH)-dione

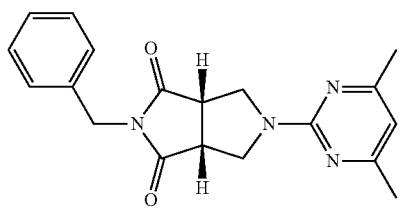 [SMILES: Cc1cc(C)nc(N2C[C@@H]3C(=O)N(Cc4ccccc4)C(=O)[C@@H]3C2)n1]

to form (3aR,6aS)-2-benzyl-5-(4,6-dimethylpyrimidin-2-yl)octahydropyrrolo[3,4-c]pyrrole

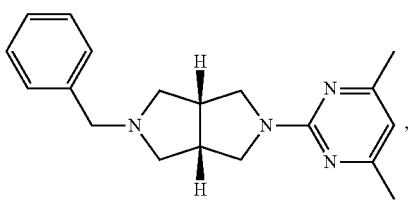 [SMILES: Cc1cc(C)nc(N2C[C@H]3CN(Cc4ccccc4)C[C@H]3C2)n1]

wherein said reduction comprises the use of one or more reagents selected from the group consisting of NaBH$_4$, PMHS, TMDS, Et$_3$SiH, Red-A1, and BH$_3$.

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

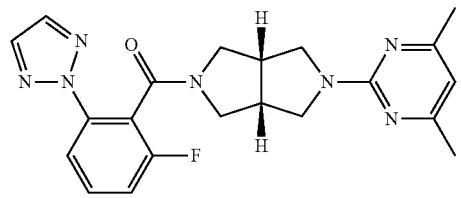 [SMILES: Cc1cc(C)nc(N2C[C@H]3CN(C(=O)c4c(F)cccc4-n4nccn4)C[C@H]3C2)n1]

said process comprising the steps described below:
a) Oxazolidination of (4,6-dimethylpyrimidin-2-yl)glycine,

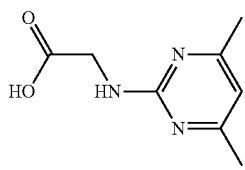

wherein said oxazolidination is characterized by the use of formaldehyde or paraformaldehyde to obtain 3-(4,6-dimethylpyrimidin-2-yl)oxazolidin-5-one

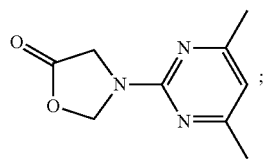

b) Reaction of 3-(4,6-dimethylpyrimidin-2-yl)oxazolidin-5-one

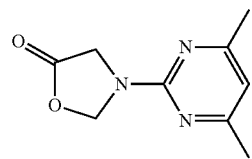

with 1-benzyl-1H-pyrrole-2,5-dione

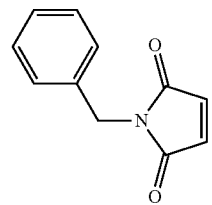 [SMILES: O=C1C=CC(=O)N1Cc1ccccc1]

at a temperature greater than 250° C. to form (3aR,6aS)-2-benzyl-5-(4,6-dimethylpyrimidin-2-yl)tetrahydropyrrolo[3,4-c]pyrrole-1,3(2H,3aH)-dione

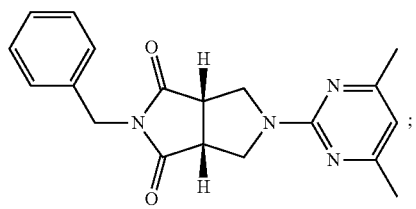 [SMILES: Cc1cc(C)nc(N2C[C@@H]3C(=O)N(Cc4ccccc4)C(=O)[C@@H]3C2)n1]

c) reduction of (3aR,6aS)-2-benzyl-5-(4,6-dimethylpyrimidin-2-yl)tetrahydropyrrolo[3,4-c]pyrrole-1,3(2H, 3aH)-dione

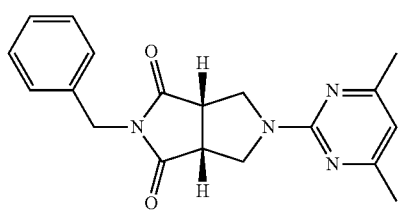 [SMILES: Cc1cc(C)nc(N2C[C@@H]3C(=O)N(Cc4ccccc4)C(=O)[C@@H]3C2)n1]

to form (3aR,6aS)-2-benzyl-5-(4,6-dimethylpyrimidin-2-yl)octahydropyrrolo[3,4-c]pyrrole

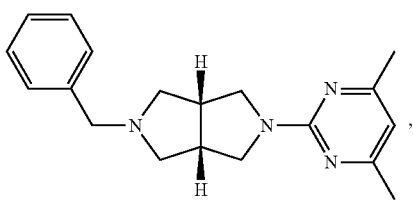 [SMILES: Cc1cc(C)nc(N2C[C@H]3CN(Cc4ccccc4)C[C@H]3C2)n1]

wherein said reduction comprises the use of one or more reagents selected from the group consisting of NaBH$_4$, PMHS, TMDS, Et$_3$SiH, Red-A1, and BH$_3$;

d) deprotection of (3aR,6aS)-2-benzyl-5-(4,6-dimethylpyrimidin-2-yl)octahydropyrrolo[3,4-c]pyrrole

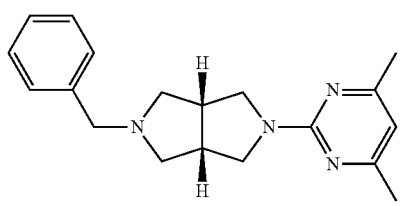 [SMILES: Cc1cc(C)nc(N2C[C@H]3CN(Cc4ccccc4)C[C@H]3C2)n1]

to form (3aR,6aS)-2-(4,6-dimethylpyrimidin-2-yl)octahydropyrrolo[3,4-c]pyrrole

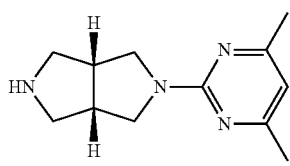 [SMILES: Cc1cc(C)nc(N2C[C@H]3CNC[C@H]3C2)n1]

by means of 10% (w/w) Pd/C and ammonium formate.

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

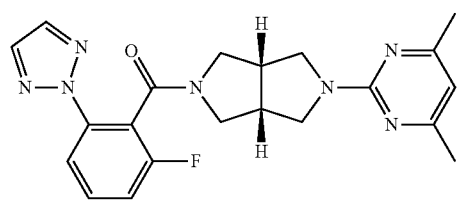 [SMILES: Cc1cc(C)nc(N2C[C@H]3CN(C(=O)c4c(F)cccc4-n4nccn4)C[C@H]3C2)n1]

said process comprising the steps described below:
a) Oxazolidination of (4,6-dimethylpyrimidin-2-yl)glycine,

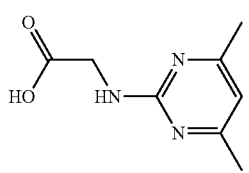

wherein said oxazolidination is characterized by the use of formaldehyde or paraformaldehyde to obtain 3-(4,6-dimethylpyrimidin-2-yl)oxazolidin-5-one

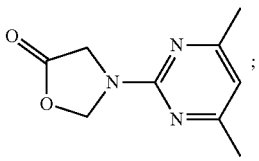

b) Reaction of 3-(4,6-dimethylpyrimidin-2-yl)oxazolidin-5-one

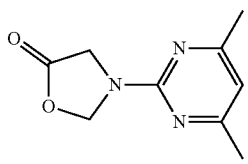

with 1-benzyl-1H-pyrrole-2,5-dione

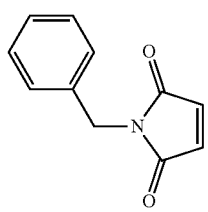 [SMILES: O=C1C=CC(=O)N1Cc1ccccc1]

at a temperature greater than 250° C. to form (3aR,6aS)-2-benzyl-5-(4,6-dimethylpyrimidin-2-yl)tetrahydropyrrolo[3,4-c]pyrrole-1,3(2H,3aH)-dione

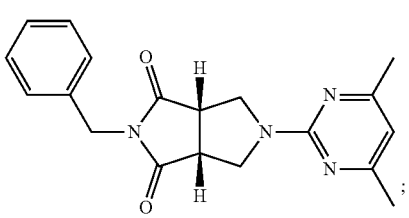

c) reduction of (3aR,6aS)-2-benzyl-5-(4,6-dimethylpyrimidin-2-yl)tetrahydropyrrolo[3,4-c]pyrrole-1,3(2H,3aH)-dione

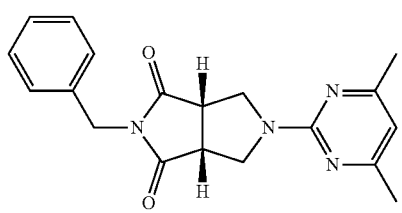 [SMILES: Cc1cc(C)nc(N2C[C@@H]3C(=O)N(Cc4ccccc4)C(=O)[C@@H]3C2)n1]

to form (3aR,6aS)-2-benzyl-5-(4,6-dimethylpyrimidin-2-yl)octahydropyrrolo[3,4-c]pyrrole

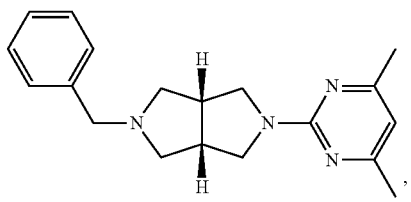 [SMILES: Cc1cc(C)nc(N2C[C@H]3CN(Cc4ccccc4)C[C@H]3C2)n1]

wherein said reduction comprises the use of one or more reagents selected from the group consisting of NaBH₄, PMHS, TMDS, Et₃SiH, Red-A1, and BH₃;

d) deprotection of (3aR,6aS)-2-benzyl-5-(4,6-dimethylpyrimidin-2-yl)octahydropyrrolo[3,4-c]pyrrole

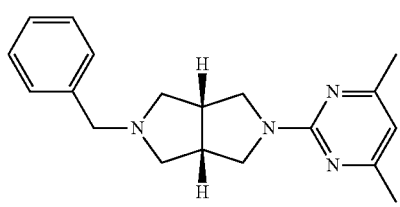 [SMILES: Cc1cc(C)nc(N2C[C@H]3CN(Cc4ccccc4)C[C@H]3C2)n1]

to form (3aR,6aS)-2-(4,6-dimethylpyrimidin-2-yl)octahydropyrrolo[3,4-c]pyrrole

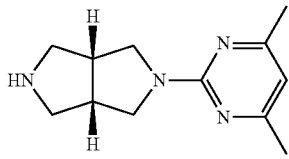

by means of 10% (w/w) Pd/C and ammonium formate;

e) Amidation of (3aR,6aS)-2-(4,6-dimethylpyrimidin-2-yl)octahydropyrrolo[3,4-c]pyrrole

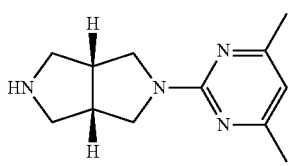 [SMILES: Cc1cc(C)nc(N2C[C@H]3CNC[C@H]3C2)n1]

with 2-fluoro-6-(2H-1,2,3-triazol-2-yl)benzoic acid

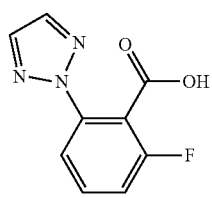 [SMILES: O=C(O)c1c(F)cccc1-n1nccn1]

by means of SOC 2 to form (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

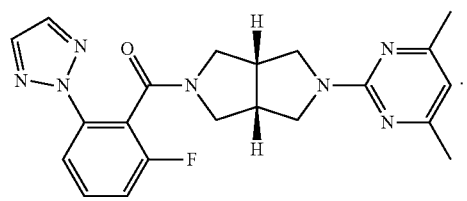 [SMILES: Cc1cc(C)nc(N2C[C@H]3CN(C(=O)c4c(F)cccc4-n4nccn4)C[C@H]3C2)n1]

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

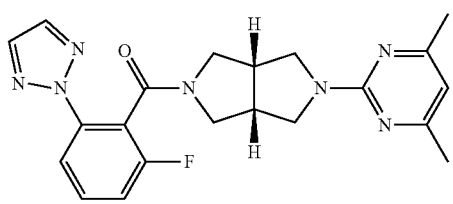 [SMILES: Cc1cc(C)nc(N2C[C@H]3CN(C(=O)c4c(F)cccc4-n4nccn4)C[C@H]3C2)n1]

said process comprising the steps described below:

a) Oxazolidination of (4,6-dimethylpyrimidin-2-yl)glycine,

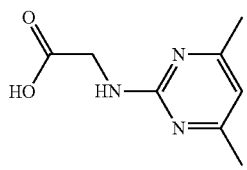

wherein said oxazolidination is characterized by the use of formaldehyde or paraformaldehyde to obtain 3-(4,6-dimethylpyrimidin-2-yl)oxazolidin-5-one

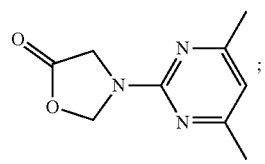

b) reaction of 3-(4,6-dimethylpyrimidin-2-yl)oxazolidin-5-one

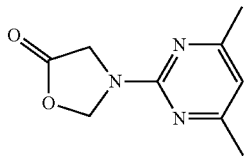

with 1H-pyrrole-2,5-dione

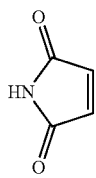

at a temperature greater than 250° C. to form (3aR,6aS)-5-(4,6-dimethylpyrimidin-2-yl)tetrahydropyrrolo[3,4-c]pyrrole-1,3(2H,3aH)-dione

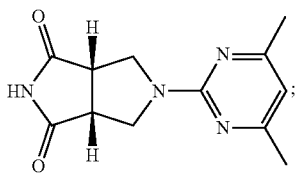 [SMILES: Cc1cc(C)nc(N2C[C@@H]3C(=O)NC(=O)[C@@H]3C2)n1]

c) reduction of (3aR,6aS)-5-(4,6-dimethylpyrimidin-2-yl)tetrahydropyrrolo[3,4-c]pyrrole-1,3(2H,3aH)-dione

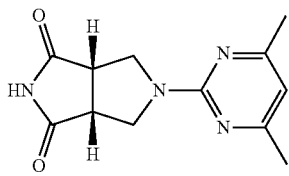 [SMILES: Cc1cc(C)nc(N2C[C@@H]3C(=O)NC(=O)[C@@H]3C2)n1]

to form (3aR,6aS)-2-(4,6-dimethylpyrimidin-2-yl)octahydropyrrolo[3,4-c]pyrrole

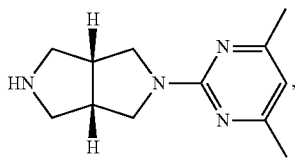 [SMILES: Cc1cc(C)nc(N2C[C@H]3CNC[C@H]3C2)n1]

wherein said reduction comprises the use of one or more reagents selected from the group consisting of NaBH$_4$, PMHS, TMDS, Et$_3$SiH, Red-A1, and BH$_3$.

Another embodiment of the invention is a process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

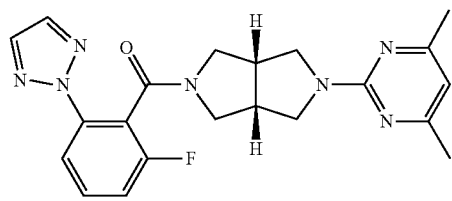 [SMILES: Cc1cc(C)nc(N2C[C@H]3CN(C(=O)c4c(F)cccc4-n4nccn4)C[C@H]3C2)n1]

said process comprising the steps described below:
a) Oxazolidination of (4,6-dimethylpyrimidin-2-yl)glycine,

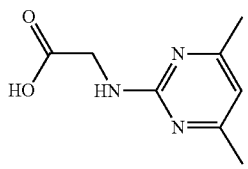

wherein said oxazolidination is characterized by the use of formaldehyde or paraformaldehyde to obtain 3-(4,6-dimethylpyrimidin-2-yl)oxazolidin-5-one

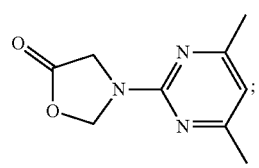

b) reaction of 3-(4,6-dimethylpyrimidin-2-yl)oxazolidin-5-one

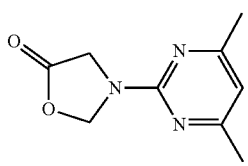

with 1H-pyrrole-2,5-dione

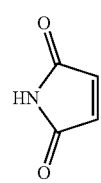

at a temperature greater than 250° C. to form (3aR,6aS)-5-(4,6-dimethylpyrimidin-2-yl)tetrahydropyrrolo[3,4-c]pyrrole-1,3(2H,3aH)-dione

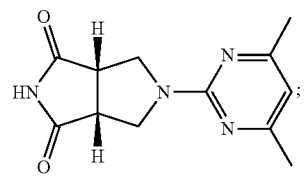 [SMILES: Cc1cc(C)nc(N2C[C@@H]3C(=O)NC(=O)[C@@H]3C2)n1]

c) reduction of (3aR,6aS)-5-(4,6-dimethylpyrimidin-2-yl)tetrahydropyrrolo[3,4-c]pyrrole-1,3(2H,3aH)-dione

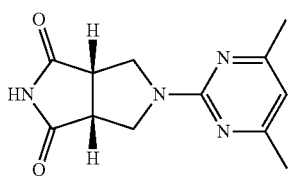 [SMILES: Cc1cc(C)nc(N2C[C@@H]3C(=O)NC(=O)[C@@H]3C2)n1]

to form (3aR,6aS)-2-(4,6-dimethylpyrimidin-2-yl)octahydropyrrolo[3,4-c]pyrrole

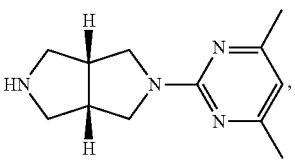 [SMILES: Cc1cc(C)nc(N2C[C@H]3CNC[C@H]3C2)n1]

wherein said reduction comprises the use of one or more reagents selected from the group consisting of NaBH$_4$, PMHS, TMDS, Et$_3$SiH, Red-A1, and BH$_3$.

e) Amidation of (3aR,6aS)-2-(4,6-dimethylpyrimidin-2-yl)octahydropyrrolo[3,4-c]pyrrole

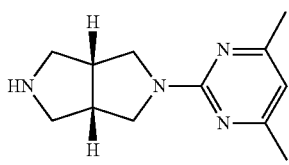 [SMILES: Cc1cc(C)nc(N2C[C@H]3CNC[C@H]3C2)n1]

with 2-fluoro-6-(2H-1,2,3-triazol-2-yl)benzoic acid

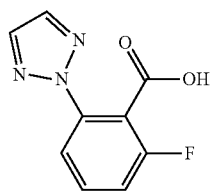 [SMILES: O=C(O)c1c(F)cccc1-n1nccn1]

by means of SOCl$_2$ to form (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

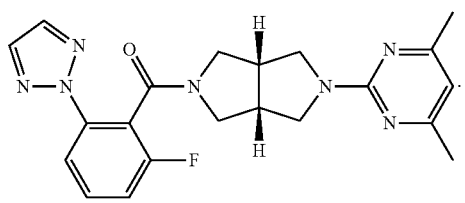 [SMILES: Cc1cc(C)nc(N2C[C@H]3CN(C(=O)c4c(F)cccc4-n4nccn4)C[C@H]3C2)n1]

Another embodiment of the invention is a compound which is 3-(4,6-dimethylpyrimidin-2-yl)oxazolidin-5-one

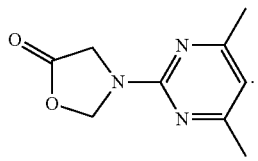

Another embodiment of the invention is a compound which is (3aR,6aS)-2-benzyl-5-(4,6-dimethylpyrimidin-2-yl)tetrahydropyrrolo[3,4-c]pyrrole-1,3(2H,3aH)-dione

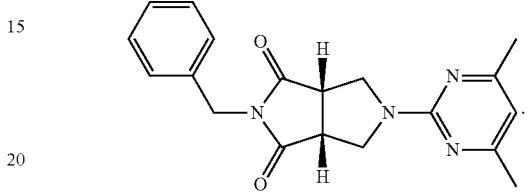

Another embodiment of the invention is a compound which is (3aR,6aS)-5-(4,6-dimethylpyrimidin-2-yl)tetrahydropyrrolo[3,4-c]pyrrole-1,3(2H,3aH)-dione

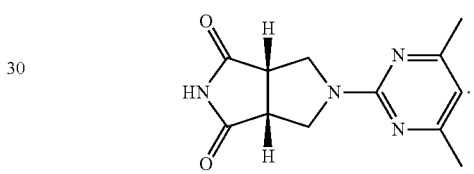

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

Definitions

The term "(((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone" means

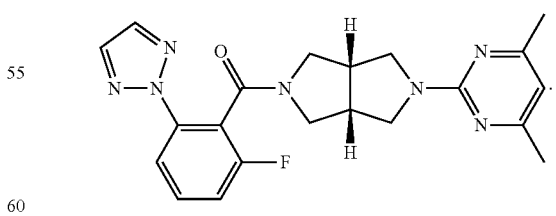

Any formula given herein is intended to represent compounds having structures depicted by the structural formula as well as certain variations or forms.

Products of the chemical reactions described in this specification may be reacted directly with additional reagents or may be separated prior to subsequent reaction.

The term "isolated" means the partial or complete separation of a reaction product from other materials in the reaction vessel. These other materials include, but are not limited to solvents, unreacted starting material, reagents used in the reaction, side-products, impurities and the products of reagents used in the reaction.

The term "preparing" means synthesizing by means of chemical processes.

Additionally, any formula given herein is intended to refer also to hydrates, solvates, and polymorphs of such compounds, and mixtures thereof, even if such forms are not listed explicitly.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, fluorine, and chlorine, such as $^2$H, $^3$H, $^{11}$C, $^{13}$C, $^{14}$C, $^{15}$N, $^{18}$O, $^{17}$O, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Those skilled in the art will recognize that compounds and reagents used in the reactions of the invention may exist as salts. The invention contemplates the use of all salts of any compound used in a reaction exemplified herein.

Examples of salts include, without limitation, sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When a compound or reagent used in a reaction of the invention contains a basic nitrogen, a salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

Those skilled in the art will recognize many reagents may be used for the removal a benzyl protecting group

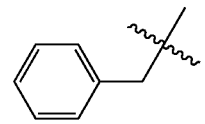 [SMILES: *Cc1ccccc1]

and reagents used in such removal are both diverse and known to the skilled practitioner. The invention contemplates the use of all common means of benzyl group removal, including those described in *Protective Groups in Organic Synthesis*, by T. W. Green, and P. G. M. Wuts, Wiley-Interscience, New York, 1999, 579-580, 744-747.

Examples of deprotective reagents include, but are not limited to, ammonium formate in the presence of a palladium catalyst, hydrogen gas in the presence of a palladium catalyst, formic acid, formic acid-triethylamine mixture, sodium formate, potassium formate, cyclohexene, or cyclohexadiene.

Exemplary reactions useful in methods of the invention will now be described by reference to the illustrative synthetic schemes for their general preparation below and the specific examples that follow. Those skilled in the art will recognize that reactions may be performed in any suitable solvent. Those skilled in the art will also recognize that, except where specifically limited, reactions may be performed at a wide range of temperatures. Unless otherwise specified, reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations

Herein and throughout the specification, the flowing abbreviations may be used.

| Abbreviation | Term |
|---|---|
| acac | acetylacetonate |
| Bn | benzyl |
| BOC | tert-Butylcarbamoyl |
| DCM | dichloromethane |
| DMSO | dimethylsulfoxide |
| EtOAc, or EA | ethyl Acetate |
| EtOH | ethanol |
| Et$_3$SiH | triethylsilane |
| HOAc | acetic Acid |
| HPLC | high-performance liquid chromatography |

37

-continued

| Abbreviation | Term |
|---|---|
| KHMDS | potassium hexamethyldisilylamide |
| MTBE | methyl tert-butyl ether |
| MeOH | methanol |
| OAc | acetate |
| PMHS | Poly(methylhydrosiloxane) |
| Red-Al | sodium bis(2-methoxyethoxy)aluminium hydride |
| TBAF | tetrabutylammonium fluoride |
| TEA | triethylamine |
| TFA | trifluoroacetic acid |
| THF | tetrahydrofuran |
| TMDS | 1,1,3,3-tetramethyldisiloxane |
| UPLC | ultra-pressure liquid chromatography |

EXAMPLES

In obtaining the compounds described in the examples below and the corresponding analytical data, the following experimental and analytical protocols were followed unless otherwise indicated.

Unless otherwise stated, reaction mixtures were stirred at room temperature (rt) under a nitrogen atmosphere. Where mixtures, solutions, and extracts were "concentrated", they were typically concentrated under reduced pressure. Reactions under microwave irradiation conditions were carried out in a Biotage Initiator or CEM Discover instrument.

Normal-phase flash column chromatography (FCC) was performed on silica gel ($SiO_2$) using prepackaged cartridges, eluting with the indicated solvents.

Mass spectra (MS) were obtained on either Bruker QTOF, Waters QTOF Ultima instruments using electrospray ionization (ESI) in positive mode unless otherwise indicated, or on a Waters GC-TOF using electronic impact (EI). Calculated (calcd.) mass corresponds to the exact mass.

Nuclear magnetic resonance (NMR) spectra were obtained on Bruker spectrometers. The format of the $^1H$ NMR data below is: chemical shift in ppm downfield of the tetramethylsilane reference (multiplicity, coupling constant J in Hz, integration).

Chemical names were generated using ChemDraw Ultra 6.0.2 (CambridgeSoft Corp., Cambridge, MA) or ACD/Name Version 9 (Advanced Chemistry Development, Toronto, Ontario, Canada).

General Scheme

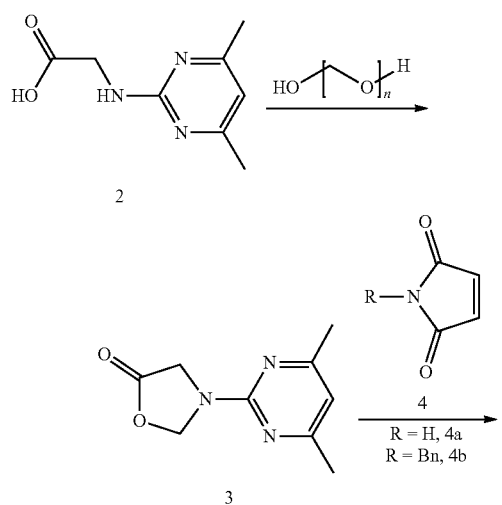

38

-continued

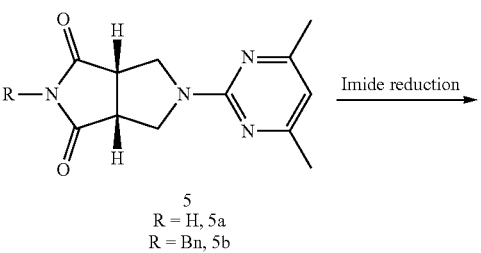

5
R = H, 5a
R = Bn, 5b

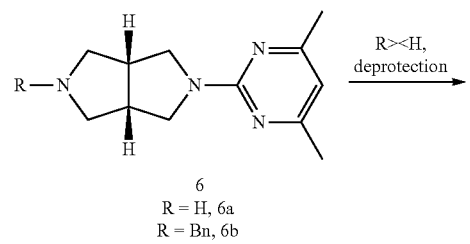

6
R = H, 6a
R = Bn, 6b

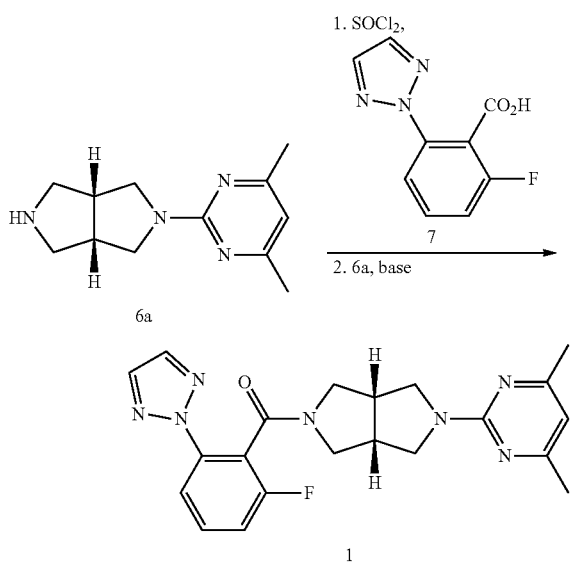

Example 1: Formation of Compound 3 from Compound 2

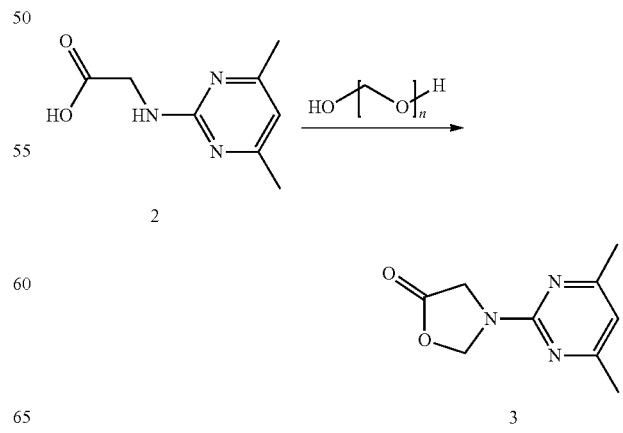

Example 1a: Batch Mode in Toluene Using Paraformaldehyde with Isolation

To a 10 L jacketed reactor were added compound 2 (496.10 g) and toluene (7.44 L). The reaction mixture was heated to 65° C. and subsequently charged with paraformaldehyde (1.2 equiv, 98.65 g). While stirring with a strong nitrogen flow, conversion was followed up by FTIR. After 23 hours reaction stalled. More paraformaldehyde (0.45 equiv, 36.99 g) was charged. After 20 hours reaction was complete according to FTIR. The reaction mixture was filtered to remove unreacted 2 and leftovers of paraformaldehyde. The mother liquor was distilled to dryness to give compound 3 (528.97 g, yield: 99%). $^1$H NMR (400 MHz, CDCl$_3$) δ 6.48 (s, 1H), 5.64 (s, 2H), 4.27 (s, 2H), 2.33 (s, 6H); $^{13}$C NMR (101 MHz, CDCl$_3$) δ 171.5 (C), 167.95 (2×C), 158.76 (CO), 111.78 (CH), 80.29 (CH$_2$), 45.01 (CH$_2$), 24.0 (2×CH$_3$). High resolution MS (EI, m/z): calcd for C$_9$H$_{11}$N$_3$O$_2$ (M)*°: 193.0851; found: 193.0847. mp. 130-135° C. (dec.).

Example 1b: Alternative Synthesis—with Aqueous Solution of Formaldehyde

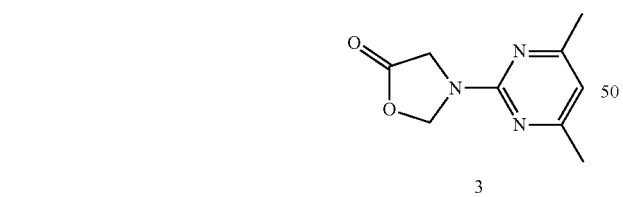

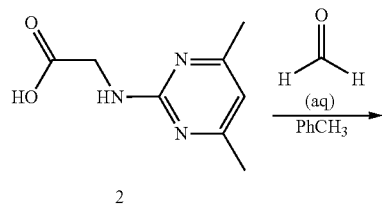

A reactor of 25 mL was charged with compound 2 (500 mg), toluene (5 mL) and aqueous solution of formaldehyde (13.31 mol/l, 4 equiv) at room temperature. To the reactor was attached a Dean-Stark apparatus and the solution was heated to 120° C. After 1 h the reaction mixture became a homogeneous solution from a heterogeneous mixture and it was cooled to 25° C. The content of the reactor was transferred to a separating funnel and diluted with ethyl acetate (30 mL). The organic layer was washed with water and brine solution followed by drying on MgSO$_4$. Removal of solvent in vacuo provided product 3 in 80% yield.

Example 2: Formation of Compound 5b (R=Bn) from Compound 3

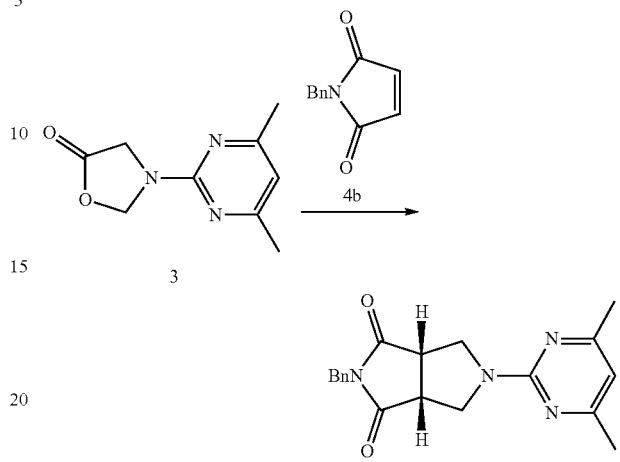

Example 2a: Screening in Toluene Under Various Flow Mode Conditions

A solution of compound 3 and compound 4b (1 equiv each) in toluene (4 L/mole) was delivered to the flow set up by a syringe pump (Isco 250D).

The solution was preheated in a coil of 1.7 mm id. and the reaction took place in a coil of 4 mm i.d with a length and flow rate to reach a residence time of 5 minutes. The reaction temperature was controlled by a heat-exchanger. The preheating unit, and reactor coil were all made from stainless steel and placed in the heat-exchanger to obtain a uniform reaction temperature. The process pressure was adjusted at 10 bar above vapour pressure of toluene with a back pressure regulator (Swagelock). At the outlet the reaction mixture was cooled in a stainless steel tube in tube (id. of 1.7 mm) to 60° C. and depressurized to atmospheric pressure before UPLC analysis. A fast temperature screening demonstrates the reaction does not occur before 200° C. and needs a temperature above 250° C. (see chart below). The kinetics are very fast at 300° C. (<2 min) and the product is stable for at least 5 min.

|       | % in-situ yield (5b) or % unconverted (3, 4b) | | |
| --- | --- | --- | --- |
| ° C.  | 3  | 4b | 5b |
| 25    | 98 | 2  | —  |
| 200   | 97 | 2  | 1  |
| 250   | 74 | 2  | 21 |
| 300   | 5  | —  | 78 |
| 350   | 5  | —  | 80 |

Example 2b: Reaction Kinetics with 1.5 Equiv Compound 4b

A second series of experiments using the same device than the one described in example 2a shows that the reaction is complete in about 4 minutes at 275° C., and in less than 2 minutes at 300° C. The compound 5b is stable under these conditions at 300° C. for at least 5 minutes (see charts below).

| | % in-situ yield (5b) or % unconverted (3, 4b) | | |
|---|---|---|---|
| min | 3 | 4b | 5b |
| Temperature: 275° C. | | | |
| 0 | 100 | 100 | 0 |
| 1 | 46 | 50 | 54 |
| 1.5 | 27 | 35 | 66 |
| 2 | 17 | 28 | 77 |
| 2.5 | 11 | 23 | 83 |
| 3 | 7 | 19 | 85 |
| 4 | 3 | 15 | 89 |
| 5 | 2 | 13 | 90 |
| Temperature: 300° C. | | | |
| 0 | 100 | 100 | 0 |
| 1 | 4 | 16 | 86 |
| 1.5 | 1 | 11 | 88 |
| 2 | 1 | 10 | 88 |
| 2.5 | 0 | 9 | 88 |
| 3 | 0 | 8 | 88 |
| 3.5 | 0 | 8 | 88 |
| 4 | 0 | 7 | 88 |

Example 2c: Flow Mode in Toluene with Isolation

A solution of compound 3 (1 mole) and compound 4b (1.5 or 1.25 equiv) in toluene (4 L/mole) was pumped throughout the flow system described in the example 2a with a flow such as to reach the desired time at the desired temperature described in the table below. After cooling, the solution was collected, partially evaporated under reduced pressure to a final concentration of 0.8 L/mole and crystallized at 0° C. for 5 hours. The solid (compound 5b) was filtered, washed and dried.

| Temperature (° C.) | Residence time (min) | Equiv 4b | % in-situ yield 5b | % isolated yield 5b |
|---|---|---|---|---|
| 275 | 6 | 1.5 | 87.1 | 82.2 |
| 300 | 3.5 | 1.5 | 87.9 | 73.8 |
| 275 | 6 | 1.25 | 92.1 | 80.7 |
| 300 | 3.5 | 1.25 | 89.1 | 78.2 |

$^1$H NMR (400 MHz, CDCl$_3$) δ 7.27-7.29 (m, 2H), 7.22-7.26 (m, 3H), 6.35 (s, 1H), 4.62 (s, 2H), 4.41-4.44 (m, 2H), 3.56-3.62 (m, 2H), 3.42-3.44 (m, 2H), 2.288 (s, 6H); $^{13}$C NMR (101 MHz, CDCl$_3$) δ 178.18 (2×CO), 167.36 (2×C), 161.08 (C), 135.58 (C), 128.74 (2×CH), 128.55 (2×CH), 127.98 (CH), 110.47 (CH), 48.88 (2×CH$_2$), 44.61 (2×CH), 42.85 (CH$_2$), 24.08 (2×CH$_3$). High resolution MS (ES, m/z): calcd for C$_{19}$H$_{21}$N$_4$O$_2$ (M+H)$^+$: 337.1665; found: 337.1666. m.p.=162° C.

Example 3: Formation of Compound 5a from Compound 3 and Compound 4a

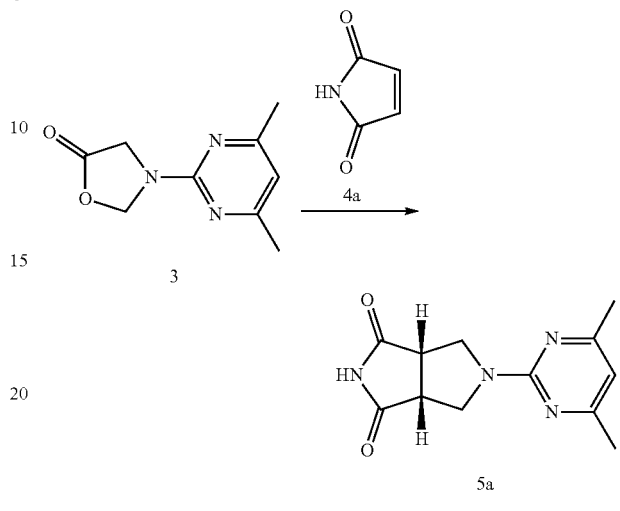

1.00 g (5.18 mmol) of compound 3, 777 mg (7.76 mmol) of compound 4a and 12 ml of toluene-d$_8$ were placed in a microwave vial. The vial was sealed and heated to 250° C. for about an hour before being cooled to room temperature. NMR analysis of the reaction mixture using 1,3,5-trimethoxybenzene as internal standard reveals that the compound 5a was formed in 45% yield. The compound 5a was isolated and purified as a solid by flash chromatography. $^1$H NMR (400 MHz, METHANOL-d$_4$) δ=6.47 (s, 1H), 4.83 (br s, 1H), 4.29 (d, J=10.1 Hz, 2H), 3.59-3.47 (m, 4H), 2.29 (s, 6H). $^{13}$C NMR (101 MHz, METHANOL-d$_4$) δ=182.26 (2×C), 169.15 (2×C), 162.62 (C), 111.33 (CH), 50.04 (2×CH$_2$), 47.24 (2×CH), 23.91 (2×CH$_3$). High resolution MS (ES, m/z): calcd for C$_{12}$H$_{15}$N$_4$O$_2$ (M+H)$^+$: 247.1195; found: 247.1189.

Example 4: Formation of Compound 5b from Compound 2

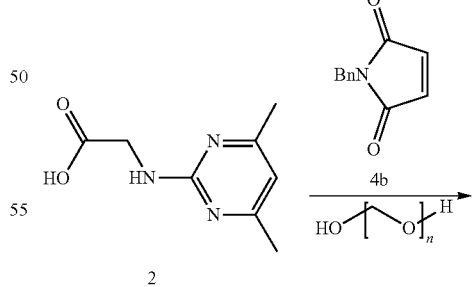

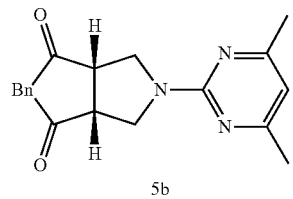

Example 4a: One-Pot Reaction in Microwave (MW) Vial

To a microwave vial (10 mL) were added compound 2 (250 mg), compound 4b, paraformaldehyde and toluene-d$_8$ and 1,4-dichlorobenzene (51 mg, 0.25 equiv); the amounts of compound 4b, paraformaldehyde and toluene-d$_8$ are reported in the table below. The tube was sealed with a cap, placed in a Biotage microwave oven and heated to 250° C. for 1 h while stirring. After 1 h the reaction vial was cooled to room temperature and a sample was analyzed by $^1$H NMR to calculate the in-situ yield. Following are the results of different experiments.

| S. No | Equiv 4b | Equiv paraformaldehyde | Toluene-d$_8$ (L/kg) | % in-situ yield 5b |
|---|---|---|---|---|
| 1 | 1 | 1.5 | 16 | 81 |
| 2 | 1.25 | 1.5 | 16 | 84 |
| 3 | 1.5 | 1.5 | 16 | 91 |
| 4 | 1 | 1.5 | 12 | 69 |
| 5 | 1 | 1.5 | 8 | 58 |
| 6 | 1 | 1.2 | 16 | 71 |

Example 4b: One-Pot Reaction in Flow Mode

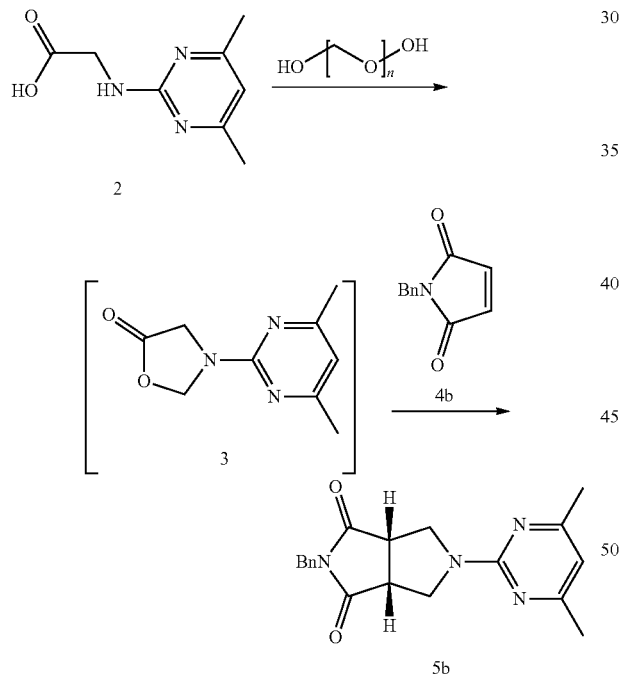

A mixed suspension of compound 2 (1 mole), paraformaldehyde (1.3 mole/mole) and compound 4b (1.4 mole/mole) in toluene (4 L/mole) was delivered to a flow set up by a syringe pump (Isco 250D).

The suspension was preheated in a coil (1.7 mm id.) and a telescoped reaction took place in a coil (1.7 mm i.d) with a length defined by the desired residence time and flow rates. The temperature for the first reaction (formation of compound 3) was controlled by a first heat-exchanger and the temperature for the second reaction formation of compound 5b) was controlled by a second heat-exchanger. The pre-heating unit, and reactor coils were all made from stainless steel and placed in two heated zones to obtain a uniform reaction temperature. The process pressure was adjusted at 10 bar above vapour pressure of toluene with a back pressure regulator (Swagelock). At the outlet the reaction mixture was cooled in a stainless steel tube in tube with id. of 1.7 mm to 60° C. and depressurized to atmospheric pressure. The product was diluted and analyzed by UPLC.

The conversion of compound 2 into compound 5b is reported in the table.

| Step 1 | | Step 2 | | % Yield relative to compound 2 | | |
|---|---|---|---|---|---|---|
| T-° C. | min | T-° C. | min | Comp. 3 | Comp. 2 | Comp. 5b |
| 180 | 8 | 300 | 3.4 | 0 | 0 | 54.2 |
| 180 | 6 | 300 | 2.6 | 0.2 | 0.2 | 54.9 |
| 180 | 4 | 300 | 1.7 | 1.1 | 2.9 | 42.0 |
| 160 | 8 | 300 | 3.4 | 0 | 0 | 62.1 |
| 160 | 6 | 300 | 2.6 | 0 | 0 | 62.6 |
| 160 | 4 | 300 | 1.7 | 1.1 | 0.8 | 53.3 |
| 200 | 4 | 300 | 2.6 | 0.1 | 0.1 | 60.8 |
| 200 | 6 | 300 | 1.7 | 1 | 0.8 | 50.7 |

Example 4c: One-Pot Reaction in Batch-Flow Mode

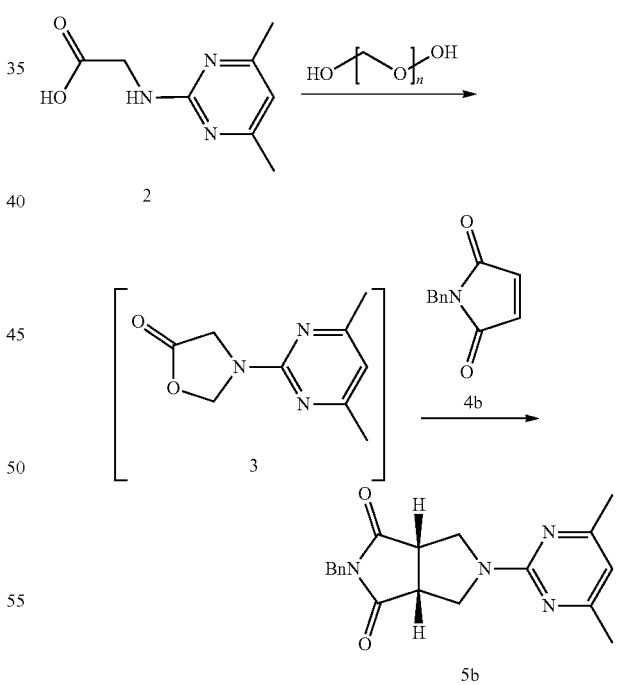

A suspension of compound 2 (1 mole), paraformaldehyde (1.5 equiv) and compound 4b (1.4 mole/mole) in toluene (4 L/mole) was heated in a closed vessel to 85° C. (0.5 bar overpressure) and stirred for two hours to reach complete conversion of 2 into 3 (see table below). After cooling, the resulting solution (25° C.) was dried over MgSO$_4$. Then used in the next step.

| Condition | UPLC (mol rel./in situ Y) | |
|---|---|---|
| | Cpd 3 | Cpd 2 |
| 0 min at 85° C. | 43 (44) | 57 (58.9) |
| 13 min | 91.9 (95.2) | 5.7 (5.9) |
| 80 min | 96.5 (102.2) | 1.3 (1.4) |
| 105 min | 96.4 (101.4) | 1.2 (1.3) |
| MgSO₄ dried solution | 91.4 | 1 |

The obtained solution of compound 3 was delivered to the flow set up by a syringe pump (Isco 250D). The suspension was preheated in a coil (1.7 mm id.) and the reaction took place in a coil (1.7 mm i.d) with a length defined by the desired residence time of 3 minutes and flow rates. The reactions temperature was controlled at 300° C. by a heat-exchanger. The preheating unit, and reactor coil were all made from stainless steel and placed in the heat-exchanger to obtain a uniform reaction temperature. The process pressure was adjusted at 10 bar above vapour pressure of toluene with a back pressure regulator (Swagelock). At the outlet the reaction mixture was cooled in a stainless steel tube in tube (id. of 1.7 mm) to 60° C. and depressurized to atmospheric pressure. The compound 5b was obtained in 66% yield.

Reaction in chlorobenzene gave the compound 5b in similar yield as in toluene.

Example 5: Formation of Compound 5a from Compound 2 and Compound 4a

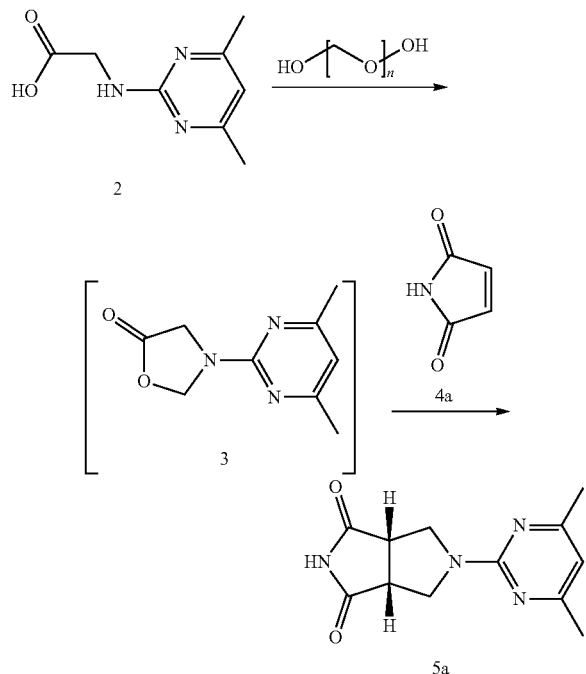

250 mg (1.38 mmol) of compound 2, 62 mg (2.07 mmol) of paraformaldehyde, 207 mg (2.07 mmol) of compound 4a and 4 ml of toluene-d₈ were placed in a microwave vial. The vial was sealed and heated to 250° C. for about an hour before being cooled to room temperature. NMR analysis of the reaction mixture using 1,3,5-trimethoxybenzne as internal standard reveals that the compound 5a was formed in 28% yield. The compound 5a was isolated and purified as a solid by flash chromatography.

Example 6: Formation of Compound 6b (R=Bn) from Compound 5b (R=Bn)

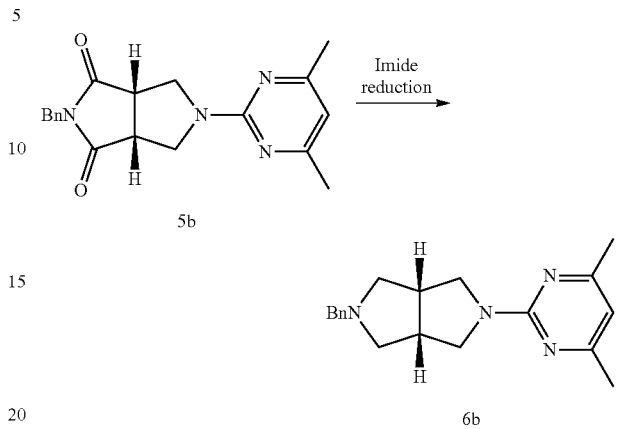

Example 6a: Reduction with NaBH₄+BF₃-THF

A 1-L reactor was charged with compound 5b (75 g), NaBH₄ (19.4 g, 2.25 equiv) and THF (375 mL). The reaction mixture was heated to 50° C. while stirring. To this was added BF₃-THF (78.1 mL, 3.1 equiv) over 2 h (Caution: very exothermic in the beginning and the intensity is reduced over the time while addition proceeds). After complete addition of BF₃-THF, the reaction was continued for 1 h. Methanol (108 mL, 12 equiv) was slowly added to the reaction mixture over 2.5 h. After stirring for additional 12 h, solvents (THF and trimethyl borate) were distilled off to reduce the volume to 1/3 and water (560 mL) followed by aqueous NaOH (47.2 mL, 4 equiv, 18.8 M) were slowly added so that pH of the reaction mixture reached ~9.6. To this was added MTBE (225 mL) and aqueous phase was discarded after phase separation. Some MTBE was distilled off (150 mL) and ethanol (203 mL) was charged to the reactor followed by further distillation removed more MTBE. After the distillation, reaction mixture was cooled to 30° C. and was seeded with some product and waited for 30 min to get the crystallization started. Once the crystallization started, water (450 mL) was added over 4 h and the reaction mixture was then cooled to 10° C. After stirring for additional 6 h the solids were filtered off using sinter funnel and the wet product was dried in oven at 50° C. for 12 h. The product compound 5 (63.3 g, 91% yield) was obtained was as an off white solid. $^1$H NMR (600 MHz, DMSO-d₆) δ=7.32-7.25 (m, 4H), 7.24-7.19 (m, 1H), 6.37 (s, 1H), 3.67 (dd, J=8.1, 11.5 Hz, 2H), 3.55 (s, 2H), 3.38 (dd, J=3.4, 11.3 Hz, 2H), 2.88-2.81 (m, 2H), 2.60 (dd, J=7.0, 9.3 Hz, 2H), 2.43 (dd, J=3.0, 9.4 Hz, 2H), 2.21 (s, 6H). $^{13}$C NMR (DMSO-d₆) δ: 166.4, 160.3, 139.1, 128.3, 128.1, 126.7, 108.3, 60.0, 58.8, 52.3, 41.0, 23.7. mp: 80° C. High resolution MS (ES, m/z): calcd for $C_{19}H_{25}N_4$ (M+H)⁺: 309.2079; found: 309.2080.

Example 6b: Reduction with NaBH₄+H₂SO₄

A 500-ml reactor was charged with compound 5b (30 g), NaBH₄ (14.5 g, 4.2 equiv) and THF (210 mL). The reaction mixture was heated to 50° C. while stirring. To this was added H₂SO₄ (10.5 mL, 2.1 equiv) over 2 h (Caution: very exothermic in the beginning and the intensity is reduced over the time while addition proceeds). After the addition of H₂SO₄ complete, the reaction was continued for 0.5 h. Methanol (73 mL, 20 equiv) was slowly added to the reaction mixture over 2 h. After stirring for additional 12 h, solvents (THF and trimethylborate) were distilled off to reduce the volume to 1/3 and water (120 mL) followed by aqueous NaOH (2.4 mL, 0.5 equiv, 18.8 M) were slowly added so that pH of the reaction mixture reached ~9.6. To this was added MTBE (210 mL) and aqueous phase was discarded after phase separation. Some MTBE was distilled off (150 mL) and ethanol (69 mL) was charged to the reactor followed by further distillation removed more MTBE. After the distillation, reaction mixture was cooled to 30° C. and was seeded with some product and waited for 30 min to get the crystallization started. Once the crystallization started, water (207 mL) was added over 4 h and the reaction mixture was then cooled to 10° C. After stirring for additional 6 h the solids were filtered off using sinter funnel and the wet product was dried in oven at 50° C. for 12 h. The product compound 6b (23.7 g, 82% yield) was obtained was as an off white solid.

Example 6c: Reduction with BH₃-THF

A 100-mL reactor was charged with compound 5b (10 g) and THF (60 mL). The reaction mixture was cooled to 10° C. while stirring. To this was added BH₃·THF (89.2 mL, 3 equiv, 1 M in THF) over 1 h. After stirring for 3 days at that temperature, methanol (60 mL) was added over 2 h and then the temperature was raised to 40° C. and stirred for 24 h. All the solvent was removed in vacuo and the crude material was dissolved in ethyl acetate and water. After phase separation, the organic layer was concentrated in vacuo to give the desired product 6b (9 g, 98% yield).

Example 6d: Reduction with Red-Al

A 25-ml reactor was charged with compound 5b (500 mg) and toluene (4 mL). The reaction mixture was heated to 60° C. while stirring. In another reactor both Red-Al (1.45 mL, 3 equiv, 60% solution in toluene) and toluene (5 mL) were heated to 60° C. while stirring. The hot Red-Al solution was then added to the above hot solution of compound 5b over 5 min. The reaction temperature was then raised to 100° C. and stirred for 2 h. After cooling to 20° C., aqueous NaOH solution was added dropwise and stirred for 2 h. Phase separation followed by removal of solvent in vacuo afforded compound 6b (480 mg, 56.7 mass % by assay, 59% yield).

Example 6e: Reduction with Silanes (Table)

Reduction with B(C₆F₅)₃/TMDS Procedure:

A 50-ml reactor was charged with compound 5b (2 g), 1,1,3,3-tetramethyldisiloxane (TMDS—6.3 mL, 6 equiv) and toluene (20 mL). The reaction mixture was heated to 60° C. while stirring. To this was added a solution of B(C₆F₅)₃ (152 mg, 5 mol %) in toluene (1 mL) and temperature was raised to 100° C. After stirring for 1 h, the reaction mixture was cooled to 25° C. and contents were transferred to a round bottom flask. Removal of solvents in vacuo provided crude compound 6b (2.07 g, 88.6% assay, 95% yield).

Reduction with Silanes Screening (Catalyst/Hydride Source):

Following the above described procedure various catalysts and silane reagents were used to reduce the compound 5b (500 mg) to 6b.

| S. No. | Catalyst (mol %) | Silane (equiv) | 6b (LC relative area %) |
|---|---|---|---|
| 1 | B(C₆F₅)₃ (1) | TMDS (5) | 0 |
| 2 | B(C₆F₅)₃ (2) | TMDS (5) | 42 |
| 3 | B(C₆F₅)₃ (3) | TMDS (5) | 89 |
| 4 | B(C₆F₅)₃ (4) | TMDS (5) | 99 |
| 5 | B(C₆F₅)₃ (5) | TMDS (5) | 99 |
| 6 | Fe₃(CO)₁₂ (5) | TMDS (5) | 38 |
| 7 | H₂PtCl₆ (1) | TMDS (5) | 25 |
| 8 | Zn(OAc)₂·2H₂O (5) | TMDS (5) | 0 |
| 9 | TBAF (1M in THF) (5) | TMDS (5) | 0 |
| 10 | Fe(acac)₃ (5) | TMDS (5) | 0 |
| 11 | Ni(acac)₂ (5) | TMDS (5) | 0 |
| 12 | Co(acac)₃ (5) | TMDS (5) | 0 |
| 13 | Mn(acac)₃ (5) | TMDS (5) | 0 |
| 14 | AlCl₃ (5) | TMDS (5) | 0 |
| 15 | KHMDS (1M in THF) (5) | TMDS (5) | 0 |
| 16 | B(C₆F₅)₃ (5) | PMHS (6) | 55 |
| 17 | Fe₃(CO)₁₂ (5) | PMHS (6) | 57 |
| 18 | H₂PtCl₆ (1) | PMHS (6) | 64 |
| 19 | H₂PtCl₆ (4) | PMHS (6) | 76 |
| 20 | Zn(OAc)₂·2H₂O (5) | PMHS (6) | 0 |
| 21 | B(C₆F₅)₃ (5) | Et₃SiH (8) | 60 |

Example 7: Formation of Compound 6a from Compound 5a, Wherein R is H

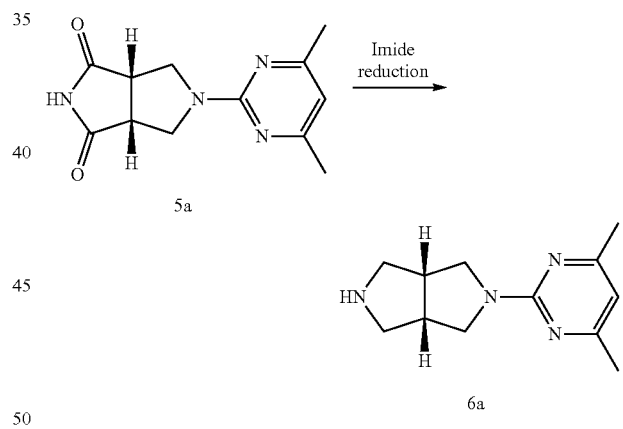

A 10 mL tube reactor was charged with compound 5a (75 mg) and THF (2 mL). The reaction mixture was cooled to 0° C. while stirring. To this was added BH₃·THF (0.91 mL, 3 equiv, 1 M in THF) slowly. The reaction mixture was slowly warmed to 50° C. with stirring and left for 4 h at that temperature. To this was slowly added methanol (0.3 mL) and stirred for 2 h. After cooling to room temperature, the crude mixture was concentrated under vacuum and the residue was redissolved in 2-methyltetrahydrofuram (3 mL) and heated to 50° C., followed by addition of aq.H₂SO₄ (0.5 mL, 4 eq, 2.28M in water). After 2 h, the solution was neutralized by addition of aq. NaOH (0.35 mL, 4.5 eq, 12.5 mass % in water) followed by phase separation and concentration in vacuo provided product 6a (60 mg, 80% assay, 72% yield).

Example 8: Formation of Compound 6a from Compound 6b

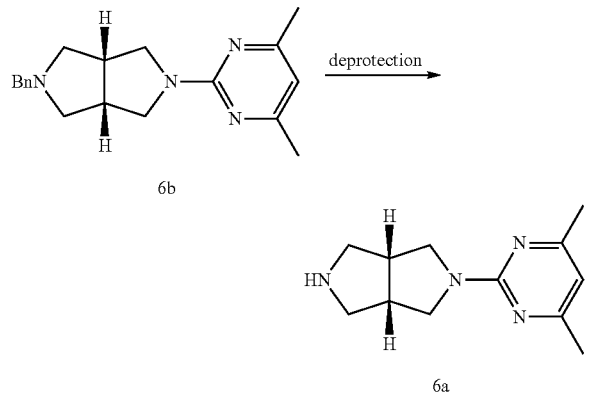

5.8 g of 10 w % Pd/C (wet) was added to a solution of 58 g (188 mmol) of compound 6b in 406 ml of methanol. The resulting suspension was heated to 60° C. before a solution of 13 g (206 mmol) of ammonium formate in 174 ml of methanol was added over an hour. The reaction mixture was then stirred 3 hours at 60° C. before being cooled to room temperature. The catalyst was filtered off and filtrate was concentrated under vacuum to obtain 40.7 g of compound 6a as a slightly yellow solid. Yield: 97%. $^1$H NMR (DMSO-$d_6$) δ: 6.35 (s, 1H), 3.68 (dd, J=11.3, 7.9 Hz, 2H), 3.32 (dd, J=11.3, 3.4 Hz, 2H), 2.93 (br dd, J=10.2, 6.0 Hz, 2H), 2.76 (br s, 2H), 2.61 (br d, J=9.4 Hz, 2H), 2.21 (s, 6H). $^{13}$C NMR (DMSO-$d_6$) δ: 166.1, 160.2, 107.9, 53.1, 51.6, 42.9, 23.4. High resolution MS (ES, m/z): calcd for $C_{12}H_{19}N_4(M+H)^+$: 219.1610; found: 219.1624. m.p.: 99-100° C.

Example 9: Formation of (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone (1) from compound 6a and compound 7

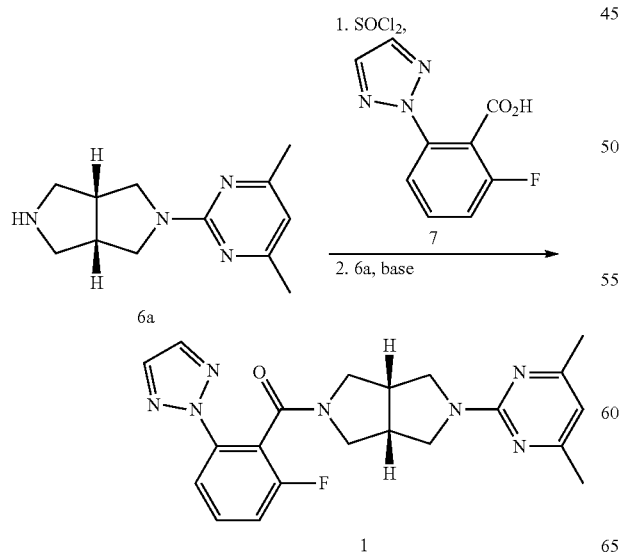

4.3 ml (60 mmol) of thionyl chloride was added to a suspension of 9.5 g (46 mmol) of compound 7 in 110 ml of toluene before being heated to 55° C. for 2.5 hours then concentrated under vacuum to a residual volume of about 100 ml (about 20 ml of solvent distilled). The resulting solution of intermediate acyl chloride in toluene was added to a well stirred biphasic mixture of 10.2 g (45.7 mmol) of compound 6a in 44 ml of toluene and 7.26 g (68.5 mmol) of sodium carbonate in 44 ml of water. The resulting biphasic mixture was stirred at 30° C. for 3.5 hours before being heating to 70° C. The water layer was discarded and the organic one was washed twice with 57 ml of water and concentrated under vacuum to a residual volume of about 64 ml. The concentrated mixture was heated to 90° C. to obtain a solution before cooling to room temperature and addition of 64 ml of cyclohexane. The resulting suspension was stirred overnight. 18.1 g of (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone (1) was obtained as a solid after filtration, wash with 12 ml of cyclohexane and 11 ml of water and drying under vacuum. Yield: 97%. $^1$H NMR (400 MHz, pyridine-$d_5$) δ ppm 2.33 (s, 12H) 2.81-2.97 (m, 4H) 3.27 (dd, J=10.6, 5.0 Hz, 1H) 3.33 (dd, J=10.5, 4.7 Hz, 1H) 3.57 (br t, J=7.1 Hz, 1H) 3.59 (br t, J=7.0 Hz, 1H) 3.67 (dd, J=11.7, 4.5 Hz, 1H) 3.70-3.75 (m, 1H) 3.75-3.82 (m, 2H) 3.82-3.98 (m, 7H) 4.11 (dd, J=12.4, 7.6 Hz, 1H) 6.29 (s, 1H) 6.29 (s, 1H) 7.19 (td, J=8.7, 1.0 Hz, 1H) 7.26 (td, J=8.6, 0.9 Hz, 1H) 7.46 (td, J=8.3, 6.2 Hz, 1H) 7.46 (td, J=8.3, 6.0 Hz, 1H) 7.90 (dt, J=8.2, 0.8 Hz, 1H) 7.90 (s, 2H) 7.98 (dt, J=8.2, 0.8 Hz, 1H) 8.04 (s, 2H). $^{13}$C NMR (101 MHz, pyridine-$d_5$) δ ppm 24.47, 24.48, 41.74, 41.82, 42.71, 42.93, 50.76, 50.82, 50.90, 51.03, 51.43, 51.62, 51.87, 52.06, 109.27, 109.44, 115.88 (br d, J=22.4 Hz), 115.89 (br d, J=22.4 Hz), 118.82 (br d, J=3.3 Hz), 118.97 (br d, J=3.3 Hz), 120.48 (d, J=24.9 Hz), 120.55 (d, J=24.6 Hz), 131.53 (br d, J=9.2 Hz), 131.54 (d, J=9.2 Hz), 137.33, 137.47, 138.04 (d, J=7.0 Hz), 138.07 (br d, J=7.0 Hz), 159.71 (d, J=245.8 Hz), 159.81 (d, J=245.4 Hz), 161.53, 161.61, 162.99 (d, J=7.3 Hz), 162.99 (d, J=7.3 Hz), 167.61, 167.63. High resolution MS (ES, m/z): calcd for $C_{21}H_{23}FN_7O$ (M+H)$^+$: 408.1943; found: 408.1946.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

What is claimed is:
1. A process of preparing (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

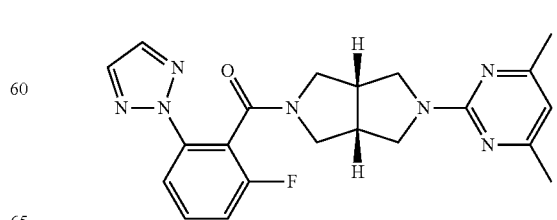

said process comprising:
Oxazolidination of (4,6-dimethylpyrimidin-2-yl)glycine,

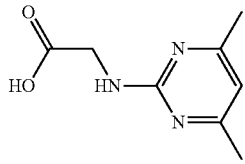

wherein said oxazolidination is characterized by the use of formaldehyde or paraformaldehyde to obtain 3-(4,6-dimethylpyrimidin-2-yl)oxazolidin-5-one

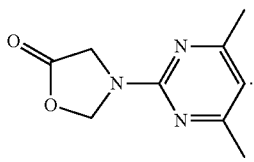

2. The process of claim 1, said process further comprising reaction of 3-(4,6-dimethylpyrimidin-2-yl)oxazolidin-5-one

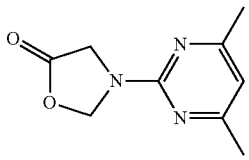

with 1-benzyl-1H-pyrrole-2,5-dione

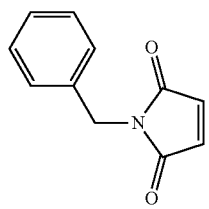 [SMILES: O=C1C=CC(=O)N1Cc1ccccc1]

at a temperature greater than 250° C. to form (3aR,6aS)-2-benzyl-5-(4,6-dimethylpyrimidin-2-yl)tetrahydropyrrolo[3,4-c]pyrrole-1,3(2H,3aH)-dione

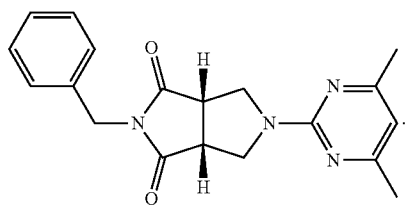 [SMILES: Cc1cc(C)nc(N2C[C@@H]3C(=O)N(Cc4ccccc4)C(=O)[C@@H]3C2)n1]

3. The process of claim 2, said process further comprising reduction of (3aR,6aS)-2-benzyl-5-(4,6-dimethylpyrimidin-2-yl)tetrahydropyrrolo[3,4-c]pyrrole-1,3(2H,3aH)-dione

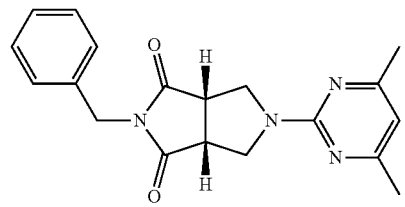 [SMILES: Cc1cc(C)nc(N2C[C@@H]3C(=O)N(Cc4ccccc4)C(=O)[C@@H]3C2)n1]

to form (3aR,6aS)-2-benzyl-5-(4,6-dimethylpyrimidin-2-yl)octahydropyrrolo[3,4-c]pyrrole

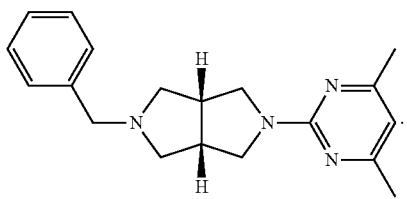 [SMILES: Cc1cc(C)nc(N2C[C@H]3CN(Cc4ccccc4)C[C@H]3C2)n1]

4. The process of claim 3, said process further comprising deprotection of (3aR,6aS)-2-benzyl-5-(4,6-dimethylpyrimidin-2-yl)octahydropyrrolo[3,4-c]pyrrole

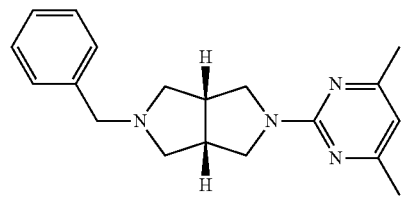 [SMILES: Cc1cc(C)nc(N2C[C@H]3CN(Cc4ccccc4)C[C@H]3C2)n1]

to form (3aR,6aS)-2-(4,6-dimethylpyrimidin-2-yl)octahydropyrrolo[3,4-c]pyrrole

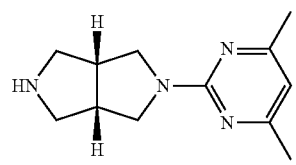 [SMILES: Cc1cc(C)nc(N2C[C@H]3CNC[C@H]3C2)n1]

by means of 10% (w/w) Pd/C and ammonium formate.

5. The process of claim 4, said process further comprising amidation of (3aR,6aS)-2-(4,6-dimethylpyrimidin-2-yl)octahydropyrrolo[3,4-c]pyrrole

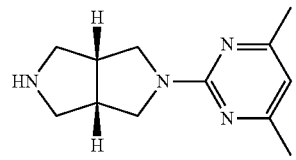 [SMILES: Cc1cc(C)nc(N2C[C@H]3CNC[C@H]3C2)n1]

with 2-fluoro-6-(2H-1,2,3-triazol-2-yl)benzoic acid

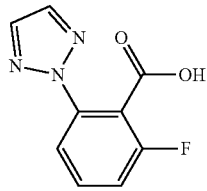 [SMILES: O=C(O)c1c(F)cccc1-n1nccn1]

by means of SOCl₂ to form (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

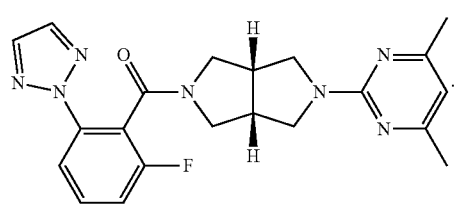 [SMILES: Cc1cc(C)nc(N2C[C@H]3CN(C(=O)c4c(F)cccc4-n4nccn4)C[C@H]3C2)n1]

6. The process of claim 1, said process further comprising reaction of 3-(4,6-dimethylpyrimidin-2-yl)oxazolidin-5-one

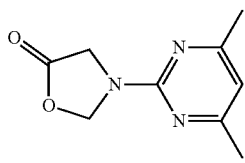

with 1H-pyrrole-2,5-dione

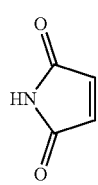

at a temperature greater than 250° C. to form (3aR,6aS)-5-(4,6-dimethylpyrimidin-2-yl)tetrahydropyrrolo[3,4-c]pyrrole-1,3(2H,3aH)-dione

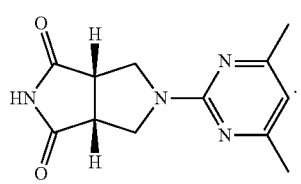 [SMILES: Cc1cc(C)nc(N2C[C@@H]3C(=O)NC(=O)[C@@H]3C2)n1]

7. The process of claim 6, said process further comprising reduction of (3aR,6aS)-5-(4,6-dimethylpyrimidin-2-yl)tetrahydropyrrolo[3,4-c]pyrrole-1,3(2H,3aH)-dione

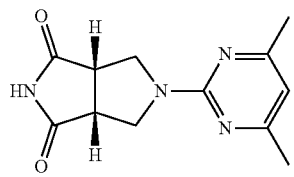 [SMILES: Cc1cc(C)nc(N2C[C@@H]3C(=O)NC(=O)[C@@H]3C2)n1]

to form (3aR,6aS)-2-(4,6-dimethylpyrimidin-2-yl)octahydropyrrolo[3,4-c]pyrrol

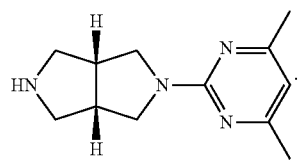 [SMILES: Cc1cc(C)nc(N2C[C@H]3CNC[C@H]3C2)n1]

8. The process of claim 7, said process further comprising amidation of (3aR,6aS)-2-(4,6-dimethylpyrimidin-2-yl)octahydropyrrolo[3,4-c]pyrrole

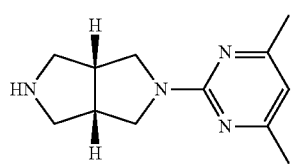

with 2-fluoro-6-(2H-1,2,3-triazol-2-yl)benzoic acid

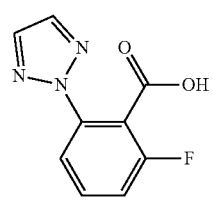 [SMILES: O=C(O)c1c(F)cccc1-n1nccn1]

by means of SOCl₂ to form (((3aR,6aS)-5-(4,6-dimethylpyrimidin-2-yl)hexahydropyrrolo[3,4-c]pyrrol-2(1H)-yl)(2-fluoro-6-(2H-1,2,3-triazol-2-yl)phenyl)methanone

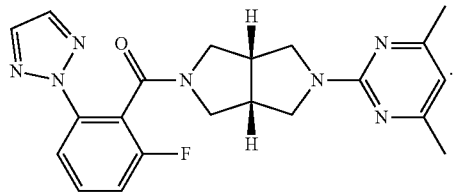 [SMILES: Cc1cc(C)nc(N2C[C@H]3CN(C(=O)c4c(F)cccc4-n4nccn4)C[C@H]3C2)n1]

9. The process of claim 2, wherein said 3-(4,6-dimethylpyrimidin-2-yl)oxazolidin-5-one is not isolated prior to reaction with said 1-benzyl-1H-pyrrole-2,5-dione.

10. The process of claim 2, wherein said 3-(4,6-dimethylpyrimidin-2-yl)oxazolidin-5-one is isolated prior to reaction with said 1-benzyl-1H-pyrrole-2,5-dione.

11. The process of claim 6, wherein said 3-(4,6-dimethylpyrimidin-2-yl)oxazolidin-5-one is not isolated prior to reaction with said 1H-pyrrole-2,5-dione.

12. The process of claim 6, wherein said 3-(4,6-dimethylpyrimidin-2-yl)oxazolidin-5-one is isolated prior to reaction with said 1H-pyrrole-2,5-dione.

13. A compound which is 3-(4,6-dimethylpyrimidin-2-yl)oxazolidin-5-one

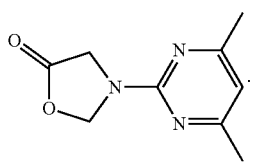

14. A compound which is (3aR,6aS)-2-benzyl-5-(4,6-dimethylpyrimidin-2-yl)tetrahydropyrrolo[3,4-c]pyrrole-1,3(2H,3aH)-dione

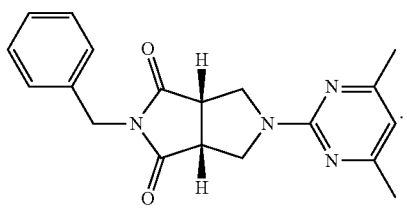 [SMILES: Cc1cc(C)nc(N2C[C@@H]3C(=O)N(Cc4ccccc4)C(=O)[C@@H]3C2)n1]

15. A compound which is (3aR,6aS)-5-(4,6-dimethylpyrimidin-2-yl)tetrahydropyrrolo[3,4-c]pyrrole-1,3(2H,3aH)-dione

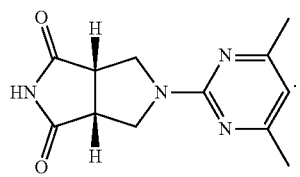 [SMILES: Cc1cc(C)nc(N2C[C@@H]3C(=O)NC(=O)[C@@H]3C2)n1]

* * * * *